United States Patent [19]
Mak et al.

[11] Patent Number: 5,731,490
[45] Date of Patent: Mar. 24, 1998

[54] MUTANT MOUSE LACKING THE EXPRESSION OF INTERFERON REGULATORY FACTOR 1 (IRF-1)

[75] Inventors: Tak W. Mak, Toronto, Canada; Tadatsugu Taniguchi, Osaka, Japan

[73] Assignee: The Ontario Cancer Institute, Toronto, Canada

[21] Appl. No.: 392,292

[22] Filed: Feb. 21, 1995

Related U.S. Application Data

[63] Continuation of Ser. No. 118,190, Sep. 9, 1993, abandoned, which is a continuation-in-part of Ser. No. 952,983, Sep. 29, 1992, abandoned.

[51] Int. Cl.⁶ .......................... C12N 15/00; C12N 15/87; C12N 15/90; C12N 5/10
[52] U.S. Cl. ................. 800/2; 800/DIG. 1; 800/DIG. 3; 800/DIG. 4; 435/172.3; 435/375
[58] Field of Search ............................. 800/2, DIG. 1, 800/DIG. 3, DIG. 4; 435/172.3, 240.2, 375; 835/70, 52, 33, 34

[56] References Cited

PUBLICATIONS

M. Frohman et al., Cell, vol. 56 (27 Jan. '89) pp. 145–147.
A. Pouricelli et al. PNAS, vol. 89 (Jan. 92) pp. 227–231.
K. Ohta et al., EMBO J., vol. 13 (#23) ('94) pp. 5754–5763.
E. Robertson, Biol. of Reprod., vol. 44 ('91) pp. 238–245.
T. Maniatis et al., *Molecular Cloning*, CSHL Press, CSH, ('82) pp. 270–294 310–328.
G. Yamada et al., PNAS, vol. 88 (Jan. '91) pp. 532–536.
M. Miyamoto et al., Cell, vol. 54 (Sep. 9, 1988) pp. 903–913.
Abdollahi, et al., "Interferon Regulatory Factor 1 Is a Myeloid Differentiation Primary Response Gene Induced by Interleukin 6 and Leukemia Inhibitory Factor: Role in Growth Inhibition," *Cell Growth & Differentation*, 2:401–407 (Aug. 1991).
Agui, et al., "Bone Marrow–Derived Progenitor T Cells Convey the Origin of Maturational Arrest From CD4⁺CD8⁺ to CD4⁻D8⁺ Thymocytes in LEC Mutant Rats," *Eur. J. Immunol.* 21:2277–2280 (1991).
American Type Culture Collection, "Catalogue of Recombinant DNA Materials," Maglott and Nierman (eds.), 3rd Edition, pp. 39–45 (1993).
Armstrong, "Cytopathic Effect Inhibition Assay for Interferon: Microculture Plate Assay," *Methods in Enzymology*, 78:381–387 (1981).
Au, et al., "Distinct Activation of Murine Interferon–α Promoter Region by IRF–1/ISFG–2 and Virus Infection," *Nucleic Acids Research*, 20(11):2877–2884 (1992).
Baribault, et al., "Embryonic Stem Cell Culture and Gene Targeting in Transgenic Mice," *Mol. Biol. Med.* 6:481–492 (1989).
Blanar, et al., "A Gamma–Interferon–Induced Factor that Binds the Interferon Response Sequence of the MHC Class 1 Gene, H–2K$^b$," *The EMBO Journal* 8(4):1139–1144 (1989).

Chan, et al., "Another View of the Selective Model of Thymocyte Selection," *Cell*, 73:225–236 (Apr. 23, 1993).
Chang, et al., "The Activation of Major Histocompatibility Complex Class I Genes By Interferon Regulatory Factor–1 (IRF–1)," *Immunogenetics*, 35:378–384 (1992).
Chauhan, et al., "Construction of a New Universal Vector for Insertional Mutagenesis by Homologous Recombination," *Gene*, 120:281–286 (1992).
Cohen, et al., "Enhancer–like Interferon Responsive Sequences of the Human and Murine (2'–5') Oligoadenylate Synthetase Gene Promoters," *The EMBO Journal* 7(5):1411–1419 (1988).
Cosgrove, et al., "Mice Lacking MHC Class II Molecules," *Cell* 66:1051–1066 (Sep. 6, 1991).
David–Watine, et al., "The Regulation and Expression of MHC Class I Genes," *Immunology Today*, 11(8):286–292 (1990).
De Maeyer, et al., "Interferons and Other Regulatory Cytokines," New York: John Wiley & Sons, Chapters 3, 5, 7, 8, 9, and 15, pp. 39–66, 91–113, 134–193, 364–379 (1988).
Doetschman, et al., "The in vitro Development of Blastocyst–Derived Embryonic Stem Cell Lines: Formation of Visceral Yolk Sac, Blood Islands and Myocardium," *J. Embryol. Exp. Morph.* 87:27–45 (1985).
Driggers, et al., "An Interferon γ–Regulated Protein That Binds the Interferon–Inducible Enhancer Element of Major Histocompatibility Complex Class I Genes," *Proc. Natl. Acad. Sci. USA*, 87:3743–3747 (May 1990).
Du, et al., "An ATF/CREB Binding Site Protein is Required for Virus Induction of the Human Interferon β Gene," *Proc. Natl. Acad. Sci. USA*, 89:2150–2154 (Mar. 1992).

(List continued on next page.)

*Primary Examiner*—Charles C. P. Rories
*Attorney, Agent, or Firm*—Marshall, O'Toole, Gerstein, Murray & Borun

[57] ABSTRACT

Interferon regulatory factor–1 (IRF-1) is implicated in the regulation of type I interferons (IFN) and cell growth. The invention is a mutant mouse lacking expression of the IRF-1 gene. Mice lacking IRF-1 did not differ from normal mice in size, behaviour, or reproductive ability. With fibroblasts derived from these mutant mice, it was shown that type I IFN induction is dramatically reduced when cells are induced by poly(I):poly(C). In contrast, no differences were found when cells are induced by New Castle Disease Virus (NDV), or induced by poly(I):poly(C) with prior treatment of IFN-β. On the other hand, the induction levels of IFN-inducible genes such as MHC class I and 2'-5' oligoadenylate synthetase (2'5'OAS) were not affected. Collectively, these results illustrate an IRF-1 independent mechanism of gene induction for type I IFN and these IFN-inducible genes. The critical role of IRF-1 in the immune system has been documented for the first time by the observation that the number of TcRαβ⁺CD4⁻CD8⁺ T cells were dramatically reduced in IRF-1 deficient mice. This phenotype may be ascribed to a thymocyte developmental defect between the double positive and single positive stages during CD8⁺ T cell ontogeny.

6 Claims, 17 Drawing Sheets

OTHER PUBLICATIONS

Enoch, et al., "Activation of the Human β–Interferon Gene Requires an Interferon–Inducible Factor," *Molecular and Cellular Biology*, 6(3):801–810 (Mar. 1986).

Evans, et al., "Establishment in Culture of Pluripotential Cells From Mouse Embryos," *Nature*, 292:154–156, (Jul. 9, 1981).

Everson, et al., "Synergism of Interleukin 7 with the Thymocyte Growth Factors Interleukin 2, Interleukin 6 and Tumor Necrosis Factor α in the Induction of Thymocyte Proliferation," *Cellular Immunology* 127:470–482 (1990).

Feng, et al., "Identification of Double–Stranded RNA–Binding Domains in the Interferon–Induced Double–Stranded RNA–Activated p68 Kinase," *Proc. Natl. Acad. Sci. USA*, 89:5447–5451 (Jun. 1992).

Flenniken, et al., "Expression of Interferon–Induced Genes in Different Tissues of Mice," *Journal of Virology*, 62(9):3077–3083 (Sep. 1988).

Frohman, et al., "Cut, Paste, and Save: New Approaches to Altering Specific Genes in Mice," *Cell*, 56:145–147 (Jan. 27, 1989).

Fu, et al., "The Proteins of ISGF–3, the Interferon α–induced Transcriptional Activator, Define a Gene Family Involved in Signal Transduction," *Proc. Natl. Acad. Sci. USA* 89:7840–7843 (Aug. 1992).

Fujita, et al., "Induction of Endogenous IFN–α and IFN–β Genes by a Regulatory Transcription Factor, IRF–1," *Nature*, 337:270–272 (Jan. 19, 1989).

Fujita, et al., "Induction of the Transcription Factor IRF–1 and Interferon–β mRNAs by Cytokines and Activators of Second–Messenger Pathways," *Proc. Natl. Acad. Sci. USA*, 86:9936–9940 (Dec. 1989).

Fujita, et al., "Involvement of a cis–element that Binds an H2TF–1/NF$_K$B like factor(s) in the virus–induced interferon–β gene Expression," *Nucleic Acids Research*, 17(9):3335–3346 (1989).

Fujita, et al., "Delimitation and Properties of DNA Sequences Required for the Regulated Expression of Human Interferon–β Gene," *Cell*, 41:489–496 (Jun. 1985).

Fujita, et al., "Interferon–β Gene Regulation: Tandemly Repeated Sequences of a Synthetic 6 bp Oligomer Function as a Virus–Inducible Enhancer," *Cell*, 49:357–367 (May 8, 1987).

Fujita, et al., "Evidence for a Nuclear Factor(s), IRF–1, Mediating Induction and Silencing Properties to Human IFN–β Gene Regulatory Elements," *The EMBO Journal*, 7(11):3397–3405 (1988).

Fung–Leung, et al., "Embryonic Stem Cells and Homologous Recombination," *Current Opinion in Immunology*, 4:189–194 (1992).

Fung–Leung, et al., "Immune Response Against Lymphocytic Choriomeningitis Virus Infection in Mice Without CD8 Expression," *J. Exp. Med.*, 174:1425–1429 (Dec. 1991).

Fung–Leung, et al., "CD8 Is Needed for Development of Cytotoxic T Cells but Not Helper T Cells," *Cell*, 65:443–449 (May 3, 1991).

Gossler, et al., "Transgenesis by Means of Blastocyst–Derived Embryonic Stem Cell Lines," *Proc. Natl. Acad. Sci. USA*, 83:9065–9069 (Dec. 1986).

Guidos, et al., "Intrathymic Maturation of Murine T Lymphocytes From CD8$^+$ Precursors," *Proc. Natl. Acad. Sci. USA*, 86:7542–7546 (Oct. 1989).

Gupta, et al., "Primary Antibody Responses to a Well–Defined and Unique Hapten are Not Enhanced by Preimmunization With Carrier: Analysis in A Viral Model," *Proc. Natl. Acad. Sci. USA*, 83:2604–2608 (Apr. 1986).

Harada, et al., "Absence of the Type I IFN System in EC Cells: Transcriptional Activator (IRF–1) and Repressor (IRF–2) Genes Are Developmentally Regulated," *Cell*, 63:303–312 (Oct. 19, 1990).

Harada, et al., "Structurally Similar but Functionally Distinct Factors, IRF–1 and IRF–2, Bind to the Same Regulatory Elements of IFN and IFN–Inducible Genes," *Cell*, 58:729–739 (Aug. 25, 1989).

Harada, et al., "Anti–Oncogenic and Oncogenic Potentials of Interferon Regulatory Factors–1 and –2," *Science*, 259:971–974 (12 Feb. 1993).

Heinz, et al., "Accommodation of Amino Acid Insertions in an α–Helix of T4 Lysozyme," *J. Mol. Biol.*, 236:869–886 (1994).

Hogan, et al., "Manipulating the Mouse Embryo: A Laboratory Manual," Cold Spring Harbor, New York: Cold Spring Harbor Laboratory, pp. i–ix, 88–267 (1986).

Ichii, et al., "Mouse 2–5A Synthetase cDNA: Nucleotide Sequence and Comparison to Human 2–5A Synthetase," *Nucleic Acids Research*, 14(24):10117 (1986).

Israel, et al., "Interferon Response Sequence Potentiates Activity of an Enhancer in the Promoter Region of a Mouse H–2 Gene," *Nature* 322: 743–746 (Aug. 21, 1986).

Ivanov, et al., "Transcription Factors in Mouse Fetal Thymus Development," *International Immunology*, 4(7):729–737 (1992).

Joyner, et al., "Production of a Mutation in Mouse En–2 Gene by Homologous Recombination in Embryonic Stem Cells," *Nature* 338:153–156 (9 Mar. 1989).

Koller, et al., "Normal Development of Mice Deficient in β$_2$M, MHC Class I Proteins, and CD8$^+$ T Cells," *Science*, 248:1227–1230 (8 Jun. 1990).

Korber, et al., "Regulation of Gene Expression by Interferons: Control of H–2 Promoter Responses," *Science*, 239:1302–1306 (11 Mar. 1988).

Kuhn, et al., "Generation and Analysis of Interleukin–4 Deficient Mice," *Science*, 254:707–710 (Nov. 1, 1991).

Leblanc, et al., "Synergism Between Distinct Enhanson Domains in Viral Induction of the Human Beta Interferon Gene," *Molecular and Cellular Biology*, 10(8):3987–3993 (Aug. 1990).

Lehmann–Grube, "Lymphocytic Choriomeningitis Virus," in *The Mouse in Biomedical Research*, Foster et al. (eds.), New York: Academic Press, Inc., vol II, Chapter 12, pp. 231–236 (1982).

Lenardo, et al., "The Involvement of NF–$_K$B in β–Inteferon Gene Regulation Reveals It Role as Widely Inducible Mediator of Signal Transduction," *Cell*, 57:287–294 (Apr. 21, 1989).

Levy, et al., "Interferon–Dependent Transcriptional Activation: Signal Transduction Without Second Messenger Involvement?" *The New Biologist*, 2(10):923–928 (Oct. 1990).

MacDonald, et al., "Different Pathways Mediate Virus Inducibility of the Human IFN–α1 and IFN–β Genes," *Cell*, 60:767–779 (Mar. 9, 1990).

Majumder, et al., "TATA–Dependent Enhancer Stimulation of Promoter Activity in Mice Is Developmentally Acquired," *Molecular and Cellular Biology*, 14(6):4258–4268 (Jun. 1994).

Maniatis, et al., *Molecular Cloning, A Laboratory Manual*, Cold Spring Harbor, New York: Cold Spring Harbor Laboratory, pp. 270–328 (1982).

Martin, "Isolation of a Pluripotent Cell Line from Early Mouse Embryos Cultured in Medium Conditioned by Teratocarcinoma Stem Cells," *Proc. Natl. Acad. Sci. USA*, 78(12):7634–7638 (Dec. 1981).

Miyamoto, et al., "Regulated Expression of a Gene Encoding a Nuclear Factor, IRF-1, That Specifically Binds to IFN–β Gene Regulatory Elements," *Cell*, 54:903–913 (Sep. 9, 1988).

Moeck, et al., "Genetic Insertion and Exposure of a Reporter Epitope in the Ferrichrome–Iron Receptor of *Escherichia coli* K–12," *Journal of Bacteriology* 176(14):4250–4259 (Jul. 1994).

Molina, et al., "Profound Block in Thymocyte Development in Mice Lacking p56$^{lck}$," *Nature*, 357:161–164 (May 14, 1992).

Naf, et al., "Multimerization of AAGTGA and GAAAGT Generates Sequences that Mediate Virus Inducibility by Mimicking an Interferon Promoter Element," *Proc. Natl. Acad. Sci. USA*, 88:1369–1373 (Feb. 1991).

Namen, et al., "B Cell Precursor Growth–Promoting Activity," *J. Exp. Med.*, 167:988–1002 (Mar. 1988).

Nikolic–Zugic, et al., "Characterization of the Subset of Immature Thymocytes Which Can Undergo Rapid In Vitro Differentiation," *Eur. J. Immunol.* 19:649–653 (1989).

Ohashi, et al., "Ablation of Tolerance and Induction of Diabetes by Virus Infection in Viral Antigen Transgenic Mice," *Cell*, 65:305–317 (Apr. 19, 1991).

Palombella et al., "Inducible Processing of Interferon Regulatory Factor–2," *Molecular and Cellular Biology*, 12(8):3325–3336 (Aug. 1992).

Pestka, et al., "Interferons and their Actions," *Ann. Rev. Biochem.*, 56:727–77 (1987).

Pine, et al., "Purification and Cloning of Interferon–Stimulated Gene Factor 2 (ISGF2): IGSF2 (IRF–1) Can Bind to the Promoters of Both Beta Interferon–and Interferon–Stimulated Genes but is not a Primary Transcriptional Activator of Either," *Molecular and Cellular Biology*, 10(6):2448–2457 (Jun., 1990).

Pine, "Constitutive Expression of an ISGF2/IRF1 Transgene Leads to Interferon–Independent Activation of Interferon–Inducible Genes and Resistance to Virus Infection," *Journal of Virology*, 66(7):4470–4478 (Jul. 1992).

Pircher, et al., "Characterization of Virus–Specific Cytoxic T Cell Clones from Allogeneic Bone Marrow Chimeras," *Eur. J. Immunol.*, 17:159–166 (1987).

Platanias, et al., "Hairy Cell Leukaemia: The Role of Alpha Interferon," *Eur. J. Cancer*, 27(4):S53–S57 (1991).

Pleiman, et al., "Organization of the Murine and Human Interleukin–7 Receptor Genes: Two mRNAs Generated by Differential Splicing and Presence of a Type I–Interferon–Inducible Promoter," *Molecular and Cellular Biology*, 11(6):3052–3059 (Jun. 1991).

Rahemtulla, et al., "Normal Development and Function of CD8+ Cells but Markedly Decreased Helper Cell Activity in Mice Lacking CD4," *Nature*, 353:180–184 (Sep. 12, 1991).

Reis, et al., "Critical Role of a Common Transcription Factor, IRF–1, in the Regulation of IFN–β and IFN–Inducible Genes," *The EMBO Journal*, 11(1):185–193 (1992).

Reyes, et al., "Isolation of a cDNA Clone for the Murine Transplantation Antigen H–2K$^b$", *Proc. Natl. Acad. Sci. USA*, 79:3270–3274 (May 1982).

Riele, et al., "Highly Efficient Gene Targeting in Embryonic Stem Cells through Homologous Recombination with Isogenic DNA Constructs," *Proc. Natl. Acad. Sci. USA*, 89:5128–5132 (Jun. 1992).

Robertson, "Using Embryonic Stem Cells to Introduce Mutations into the Mouse Germ Line," *Biology of Reproduction* 44:238–245 (1991).

Robertson, et al., "Germ–line Transmission of Genes Introduced into Cultured Pluripotential Cells by Retroviral Vector," *Nature* 323:445–448 (Oct. 2, 1986).

Roost, et al., "An Acquired Immune Suppression in Mice Caused by Infection With Lymphocytic Choriomeningitis Virus," *Eur. J. Immunol.* 18:511–518 (1988).

Rothenberg, et al., "The Development of Functionally Responsive T Cells," *Advances in Immunology*, 51:85–214 (1992).

Rudnicki, et al., "Inactivation of MyoD in Mice Leads to Up–Regulation of the Myogenic HLH Gene Myf–5 and Results in Apparently Normal Muscle Development," *Cell*, 71:383–390 (Oct. 30, 1992).

Sambrook, et al., *Molecular Cloning A Laboratory Manual*, 2nd Edition, Cold Spring Harbor, NY: Cold Spring Harbor Laboratory Press, pp. 16.10–16.14 (1989).

Schifferli, et al., "Permissive Linker Insertion Sites in the Outer Membrane Protein of 987P Fimbriae of *Escherichia coli*," *Journal of Bacteriology*, 176(4):1099–1110 (Feb. 1994).

Schwartz, et al., "A Dominant Positive and Negative Selectable Gene for Use in Mammalian Cells," *Proc. Natl. Acad. Sci. USA*, 88:10416–10420 (Dec. 1991).

Scollay, et al., "T Cell Development in the Adult Murine Thymus: Changes in the Expression of the Surface Antigens Ly2, L3T4, and B2A2 During Development from Early Precursor Cells to Emigrants," *Immunological Reviews*, 82:79–103 (1984).

Sen, et al., "Interferon–Induced Antiviral Actions and Their Regulation," *Advances in Virus Research*, 42:57–102 (1993).

Shores, et al., "Disorganization and Restoration of Thymic Medullary Epithelial Cells in T Cell Receptor–Negative Scid Mice: Evidence that Receptor–Bearing Lymphocytes Influence Maturation of the Thymic Microenvironment," *Eur. J. Immunol.*, 21:1657–1661 (1991).

Shulman, et al., "Homologous Recombination in Hybridoma Cells: Dependence on Time and Fragment Length," *Molecular and Cellular Biology*, 10(9):4466–4472 (Sep. 1990).

Smith, et al., "Inhibition of Pluripotential Embryonic Stem Cell Differentiation by Purified Polypeptides," *Nature*, 336:688–690 (Dec. 15, 1988).

Smithies, et al., "Insertion of DNA Sequences Into The Human Chromosomal β–Globin Locus by Homologous Recombination," *Nature*, 317:230–234 (Sep. 19, 1985).

Stark, et al., "Interferon Dependent Signalling Pathways: DNA elements, Transcription Factors, Mutations, and Effects of Viral Proteins," *J. Interferon Res.* 12:147–151 (1992).

Stewart, et al., "Priming: a Nonantiviral Function of Interferon," *Journal of Virology*, 7(6):792–801 (Jun. 1971).

Stewart, II, W.E., "Priming," In *The Interferon System*, New York: Springer–Verlag, pp. 233–236 (1979).

Sugita, et al., "Interferons Increase Transcription of a Major Histocompatibility Class I Gene via a 5' Interferon Consensus Sequence," *Molecular and Cellular Biology*, 7(7):2625–2630 (Jul. 1987).

Tanaka, et al., "Recognition DNA Sequences of Interferon Regulatory Factor I (IRF–1) and IRF–2, Regulators of Cell Growth and the Interferon System," *Molecular and Cellular Biology*, 13(8):4531–4538 (Aug. 1993).

Teufel, et al., "Properties of Bacteriorhodopsin Derivatives Constructed by Insertion of an Exogenous Epitope into Extramembrane Loops," *The EMBO Journal*, 12(9):3399–3408 (1993).

Thomas, et al., "Site–Directed Mutagenesis by Gene Targeting in Mouse Embryo–Derived Stem Cells," *Cell*, 51:503–512 (Nov. 6, 1987).

Uegaki, et al., "Characterization of the DNA Binding Domain of the Mouse IRF–2 Protein," *Protein Engineering*, 6(2):195–200 (1993).

Ullman, et al., "Transmission of Signals From the T Lymphocyte Antigen Receptor to the Genes Responsible for Cell Proliferation and Immune Function: The Missing Link," *Annu. Rev. Immunol.* 8:421–452 (1990).

Van Kaer, et al., "TAP1 Mutant Mice Are Deficient in Antigen Presentation, Surface Class I Molecules, and $CD4^- 8^+$ T Cells," *Cell*, 71:1205–1214 (Dec. 24, 1992).

Veals, et al., "Subunit of an Alpha–Interferon–Responsive Transcription Factor Is Related to Interferon Regulatory Factor and Myb Families of DNA–Binding Proteins," *Molecular and Cellular Biology*, 12(8):3315–3324 (Aug. 1992).

Vilcek, "Interferons," in *Peptide Growth Factors and Their Receptors. Handbook of Experimental Pharmacology*, Sporn et al. (eds.), Berlin: Springer–Verlag, Chapter 19, pp. 3–38 (1990).

Visvanathan, et al., "Double–Stranded RNA Activates Binding of NF–KB to an Inducible Element in the Human β–Interferon Promoter," *The EMBO Journal*, 8(4):1129–1138 (1989).

Von Boehmer, et al., "Lymphocyte Lineage Commitment: Instruction Versus Selection," *Cell* 73:207–208 (Apr. 23, 1993).

Watanabe, et al., "Activation of IFN–β element by IRF–1 requires a post translational event in addition to IRF–1 Synthesis," *Nucleic Acids Research*, 19(16):4421–4428 (1991).

Weissmann, et al., "The Interferon Genes," *Progress in Nucleic Acid Research and Molecular Biology*, 33:251–300 (1986).

Weisz, et al., "Human Interferon Consensus Sequence Binding Protein Is a Negative Regulator of Enhancer Elements Common to Interferon–inducible Genes," *The Journal of Biological Chemistry*, 267(35):25589–25596 (Dec. 15, 1992).

Whittemore, et al., "Postinduction Repression of the β–Interferon Gene is Mediated Through Two Positive Regulatory Domains," *Proc. Natl. Acad. Sci. USA*, 87:7799–7803 (Oct. 1990).

Williams, "Transcriptional Regulation of Interferon–Stimulated Genes," *Eur. J. Biochem*, 200:1–11 (1991).

Willman, et al., "Deletion of IRF–1, Mapping to Chromosome 5q31.1, in Human Leukemia and Preleukemic Myelodysplasia," *Science*, 259:968–971 (12 Feb. 1993).

Yamada, et al., "Specific Depletion of the B–Cell Population Induced by Aberrant Expression of Human Interferon Regulatory Factor 1 Gene in Transgenic Mice," *Proc. Natl. Acad. Sci. USA*, 88:532–536 (Jan. 1991).

Zijlstra, et al., "β2–Microglobulin Deficient Mice Lack $CD4^- 8^+$ Cytolytic T Cells," *Nature*, 344:742–746 (19 Apr. 1990).

Zinkernagel, et al., "Virally Induced Immunosuppression," *Current Opinion in Immunology*, 4:408–412 (1992).

Zinkernagel, et al., "On the Thymus in the Differentation of H–2 Self Recognition" by T Cells: Evidence for Dual Recogntion? *J. Exp. Med.*, 147:882–896 (1978).

Kimura, et al., "Involvement of the IRF–1 Transcription Factor in Antiviral Responses to Interferons," *Science*, 264:1921–1924 (Jun. 24, 1994).

S. Majumder et al. Mol. Cell. Biol., vol. 14 #6 (Jun. 1994) pp. 4258–4268.

M. Teufel et al. EMBO J. vol. 12 #9 ('93) pp. 3399–3408.

D. Schifferli: et al., J. Bacteriology, vol. 176, No. 4 (Feb. 1994) pp. 1099–1100.

D. Heinz et al. J. Mol. Biol., vol. 236 ('94) pp. 869–886.

G. Moeck et al. J. Bacteriology, vol. 176, #14 (Jul. 1994) pp. 4250–4259.

H. Riele et al. PNAS, vol. 89 (Jun. 1992) pp. 5128–5132.

M. Shulman et al. Mol. Cell. Biol., vol. 10 #9 (Sep. 1990) pp. 4466–4472.

F. Schwartz et al. PNAS, vol. 88 (Dec. 1991) pp. 10416–10420.

S. Chauhan et al. Gene. vol. 120 ('92) pp. 281–286.

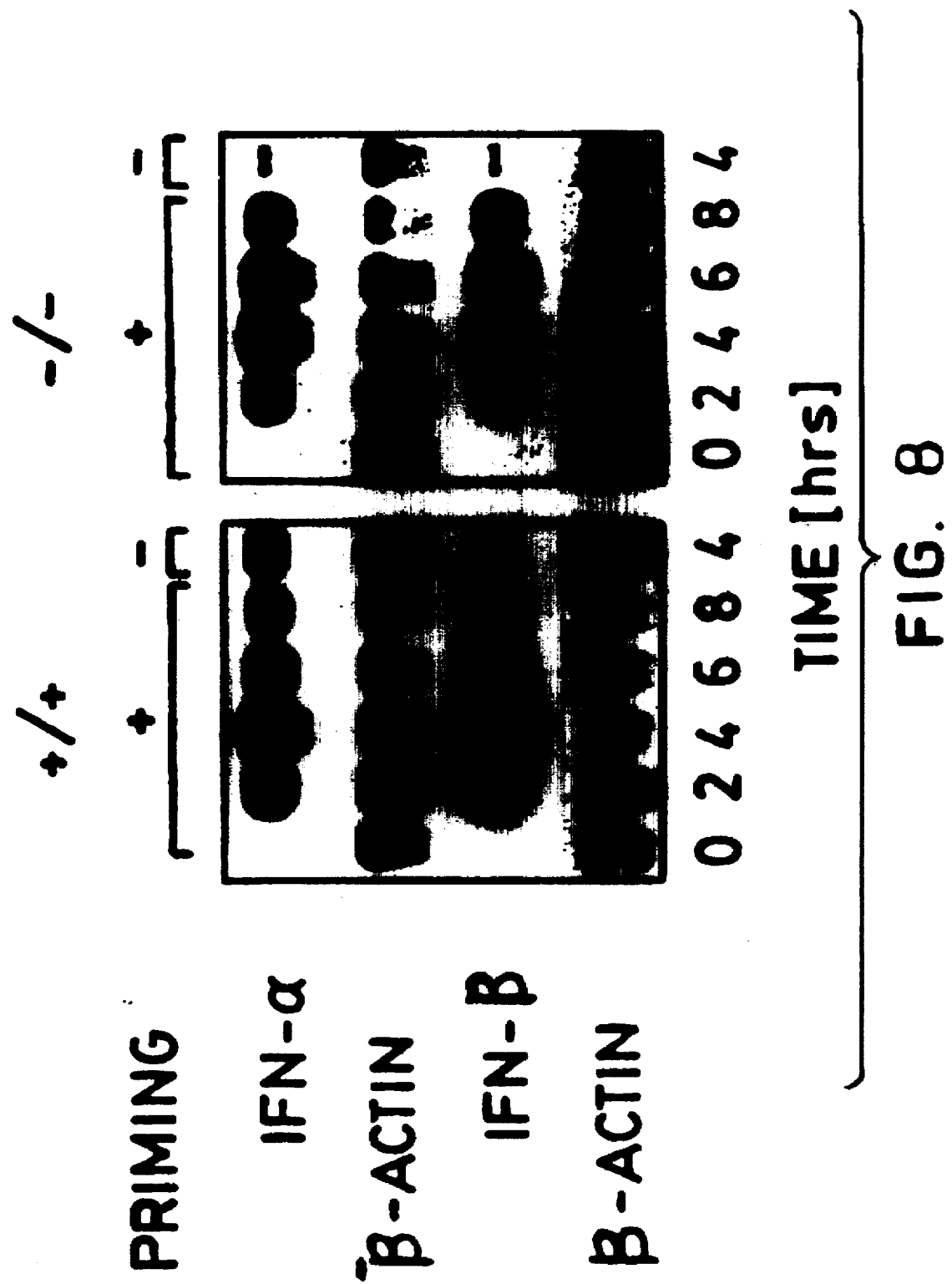

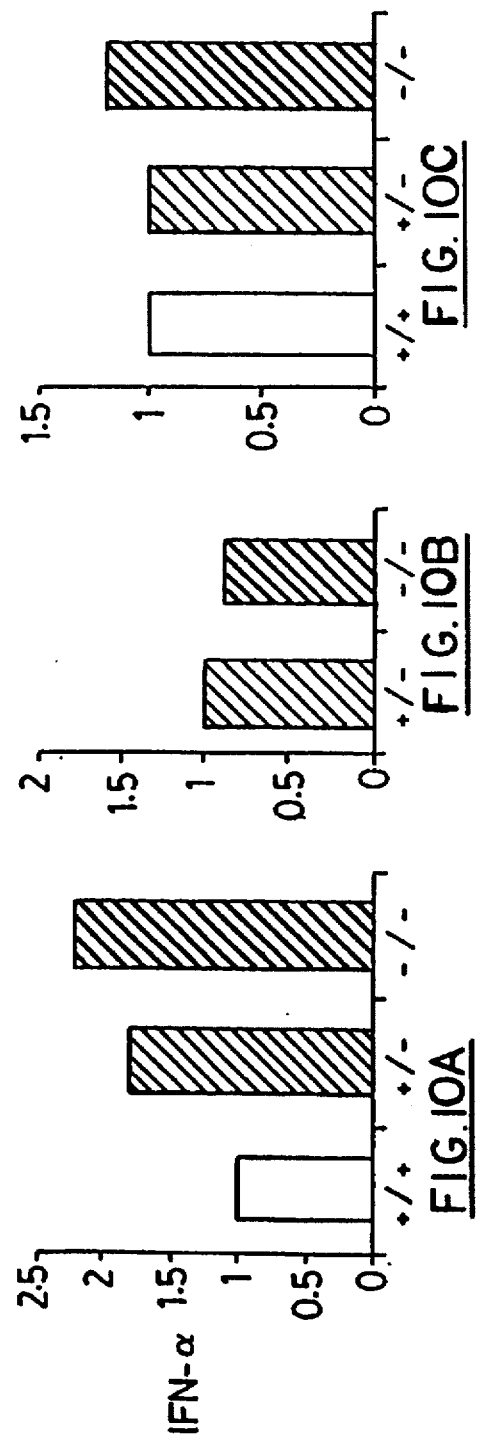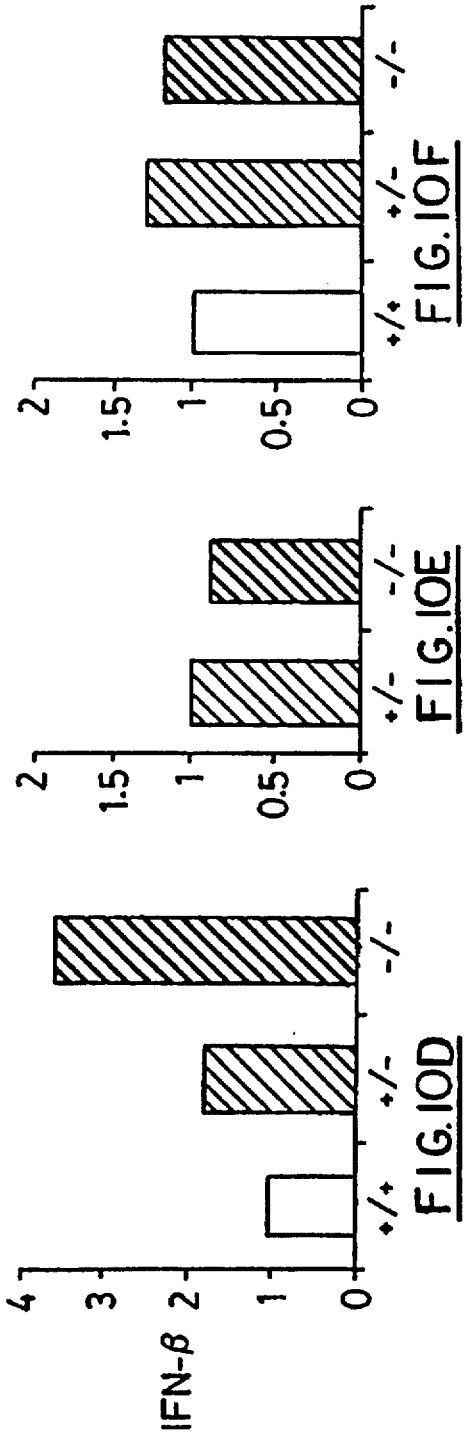

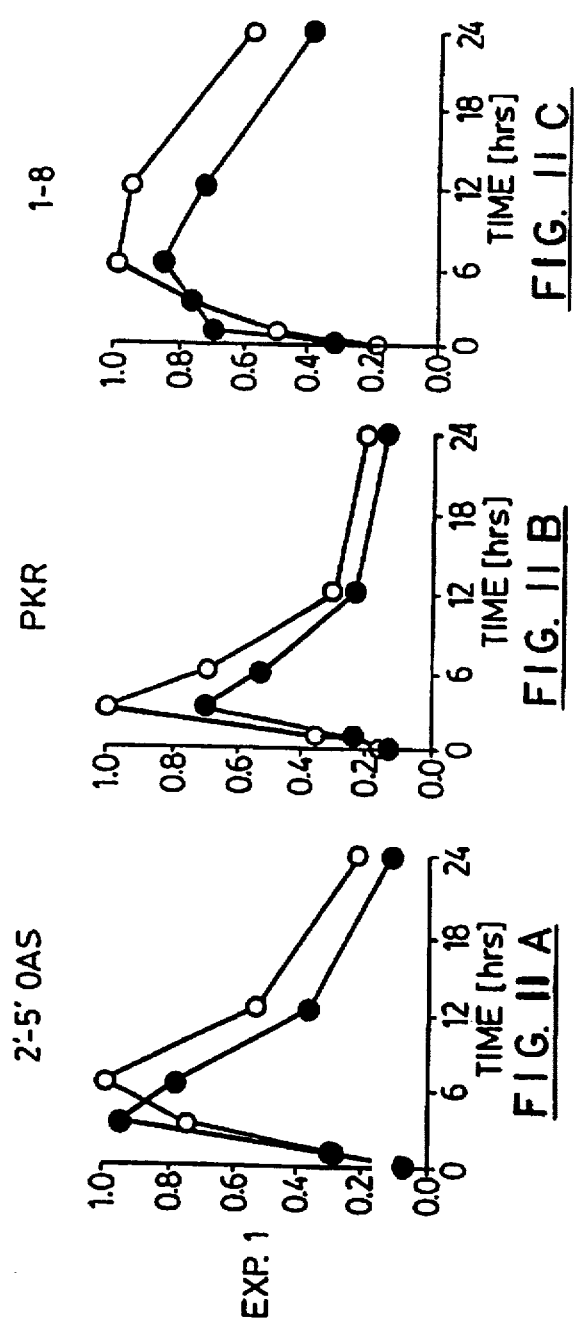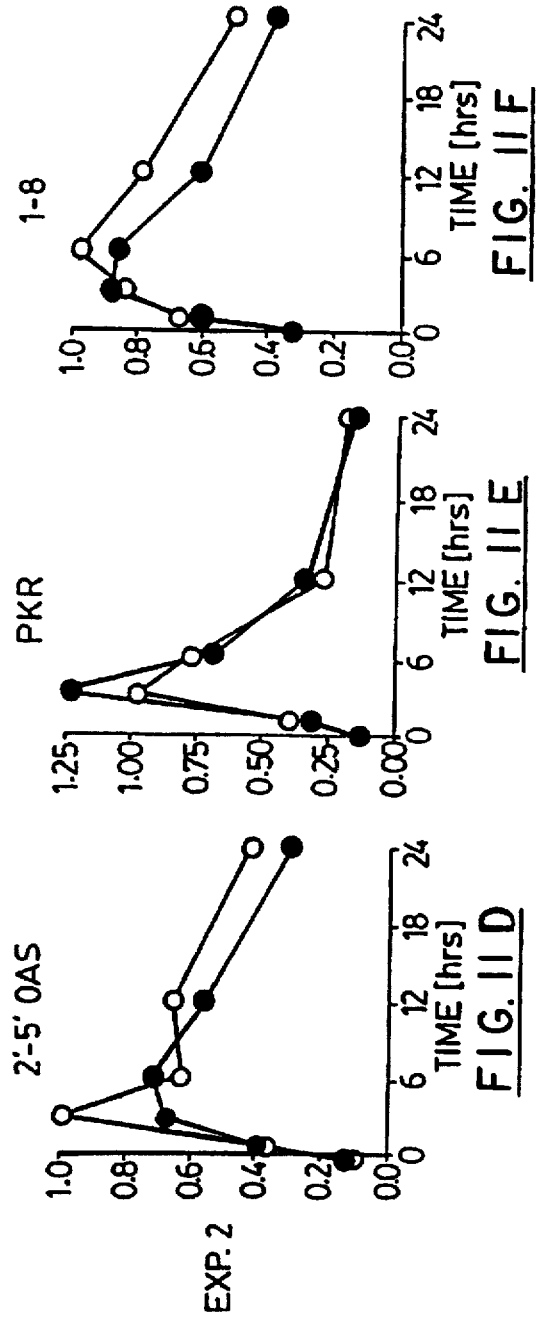

FIG. 13A +/+
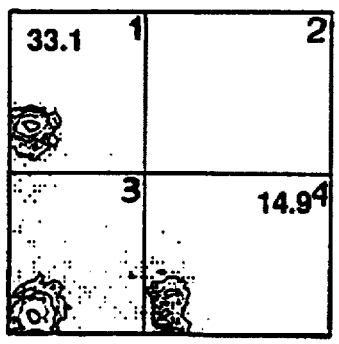
CD4 — PBL
FIG. 13B −/−
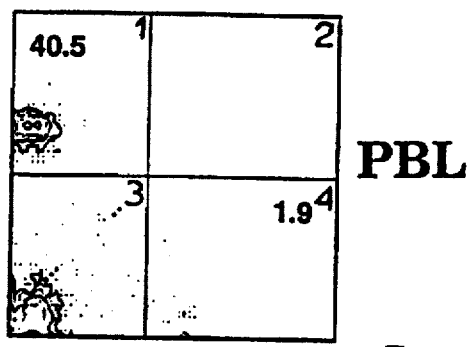
FIG. 13C
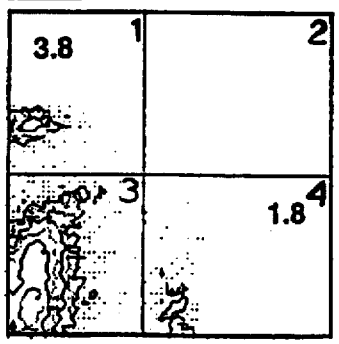
CD4 — spleen
FIG. 13D
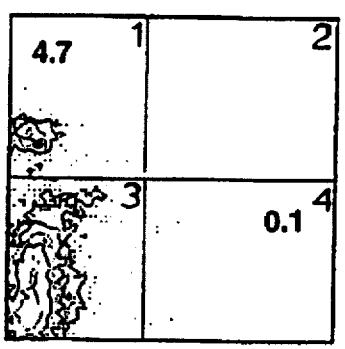
FIG. 13E
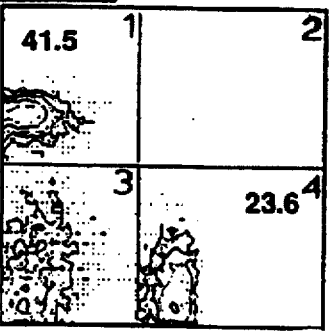
CD4 — lymph node
FIG. 13F
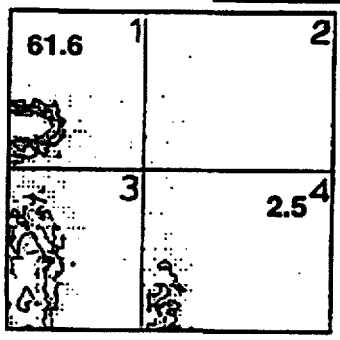
CD8

FIG. 14A +/+
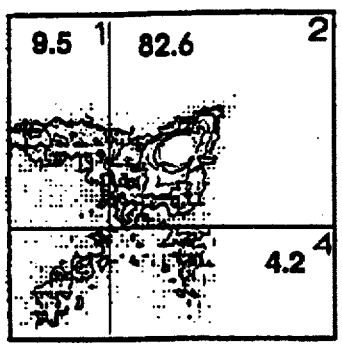
FIG. 14B −/−
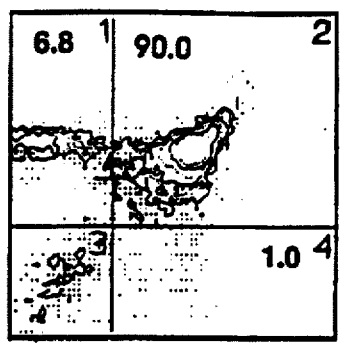
CD4 — thymus
FIG. 14C
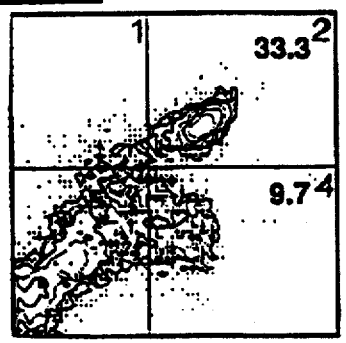
FIG. 14D
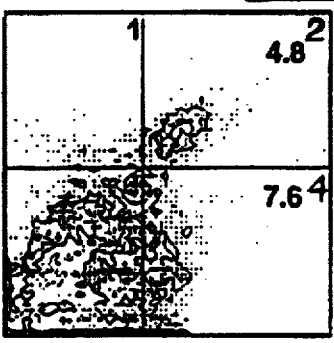
TcRαβ — thymus (CD4 depleted)
FIG. 14E
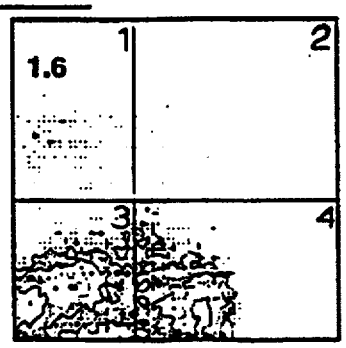
FIG. 14F
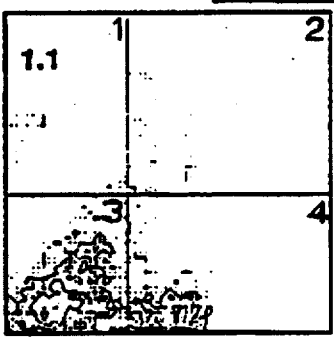
TcRγδ — thymus (CD4 depleted)
CD8

MUTANT MOUSE LACKING THE EXPRESSION OF INTERFERON REGULATORY FACTOR 1 (IRF-1)

CROSS-REFERENCE TO RELATED APPLICATIONS

This application is a file-wrapper continuation of U.S. patent application Ser. No. 08/118,190 filed Sep. 9, 1993 now abandoned, in turn a continuation-in-part of application Ser. No. 07/952,983 filed Sep. 29, 1992, now abandoned.

FIELD OF THE INVENTION

The invention is a mutant mouse lacking the expression of Interferon Regulatory Factor 1 (IRF-1). The invention is useful for the study of the response of the immune system to viral infection or other stimuli, and hence, for the development of treatments for viral diseases. The invention is also useful for the development of cancer treatments as IRF-1 has been implicated in the suppression of tumor growth.

BACKGROUND OF THE INVENTION

Type I interferons (IFNs; i.e. IFN-αs and IFN-β) are pleiotropic cytokines that are produced by many cell types in response to a variety of stimuli, such as, to viral infections, to double stranded RNA, e.g., Poly(rI):Poly(rC), and to some cytokines. On the other hand, Type II IFN, i.e. IFN-γ, is efficiently induced in T lymphocytes upon activation by antigens or by mitogens such as ConA and TPA (Stewart, 1979; Pestka et al., 1987; Weissmann and Weber, 1986; Vilcek, 1990). In addition to their potent anti-viral activity, IFNs also affect cellular growth and differentiation. In fact, IFNs exhibit anti-proliferative effects on many normal and transformed cells, suggesting that IFNs are "negative growth factors". IFNs are being used for the treatment of viral diseases and neoplasia. For example, IFNαs have been successfully used in the treatment of some types of leukemia (Palatanias and Ratain, 1991). IFNs bind to cell receptors to elicit their signals to cell interiors to induce a set of cellular genes, the so-called "IFN-inducible genes", thereby changing the physiology of the whole animal. The IFN-inducible genes include those of class I MHC (Israel et al., 1986; Sugita et al., 1987; Blanar et al., 1989; Korber et al., 1988) and 2',5'-oligoadenylate synthetase (Cohen et al., 1988).

Studies on the regulatory mechanisms of the human IFN-β gene identified two novel DNA-binding factors, Interferon Regulatory Factor 1 (IRF-1) and 2 (IRF-2) (Fujita et al., 1988; Miyamoto et al., 903–913, 1988; Harada et al., 1989). These two factors are structurally related, particularly in the N-terminal regions which confer DNA binding specificity. In fact, both factors bind to the same DNA sequence elements found within the promoters of IFN-αs, IFN-β and many IFN-inducible genes (Harada et al., ibid). A series of gene transfection studies have demonstrated that IRF-1 functions as a critical activator for IFN and IFN-inducible genes, whereas IRF-2 represses the IRF-1 effect (Fujita et al., 1989; Harada et al., 1990). In the mouse embryonal carcinoma cell line P19, in which neither of the two factors is expressed, IRF-1 cDNA expression resulted in efficient activation of endogenous or exogenous IFN-β genes. The concomitant expression of IRF-2 cDNA, however, repressed this activity (Harada et al., 1990). Expression of an IRF-1 antisense RNA in the human fibroblast line GM-637 also resulted in strong inhibition of IFN-β gene induction (Reis et al., 1992). On the other hand, lack of correlation between IRF-1 levels and induction of the IFN-β gene has been reported in HeLa cells (Pine et al.,1990), suggesting the possibility for an alternative pathway for induction of the IFN-β gene. The role of IRF-1 in IFN-mediated cellular responses has also been documented. For example, IRF-1 appears to play a role in the induction of MHC class I and 2'-5' oligoadenylate synthetase (2'5'OAS) genes by binding to the IFN-stimulated regulatory element (ISRE) where IRF-Es overlap (Harada et al., 1990; Reis et al., 1992; Au et al., 1992; Pine, 1992; reviewed by Sen and Ranshoff, 1993) In addition, IRF-1 expression in some cell lines leads to an antiviral state (Pine, 1992). However, the activation of ISRE by IFNs is also mediated by other factors such as ISGF-3, hence the existence of redundancy in ISRE activation has been suggested (reviewed by Stark and Kerr, 1992). It was recently demonstrated that restrained cell growth depends on a balance between these two competitive factors; elevated expression of IRF-2 results in transformation of NIH3T3 cells accompanied by enhanced tumorigenicity (Harada et al., 1993). This transformed phenotype, however, can be reversed by concomitant expression of IRF-1 (Harada et al, 1993). Furthermore, the human IRF-1 gene, mapping to chromosome 5q31.1, is deleted and/or inactivated at one or both alleles in 13 cases of leukaemia and preleukaemic myelodysplasia (Willman et al., 1993), implicating the IRF-1 gene a possible tumor suppressor gene.

In order to study the role of each of these transcriptional regulatory factors, IRF-1 and IRF-2, especially in an in vivo setting, perhaps one of the best approaches is to generate genetic mutant mammals such as mice that lack expression of one or both of these genes. This approach will allow the creation of new mouse strains for physiological studies as well as tissues and cell lines for in vitro examinations.

Homologous recombination in embryonic stem cells is a technology that has became realizable within the last couple of years (Fung-Leung and Mak, 1991). New strains of mice carrying specific mutations can be obtained when one combines the approach of homologous recombinations in embryonic stem cells with the technique of blastocyte injection and re-implantation. This was achieved by disruption of the coding sequence of the murine gene by homologous recombination (Smithies et al., 1985) in embryonic stem cells (Thomas and Capecchi, 1987). The embryonic stem cells (Evans and Kaufman, 1981; Martin, 1981) have the potential to contribute to all tissues including the germline when they are introduced into mouse preimplantation embryos (Gossler et al., 1986; Robertson et al., 1986). Subsequent breeding of the mice allows the generation of a new fertile mouse strain, homozygous for the genetic change. This technique may be analogously applied across mammalian species, but for practical purposes, efforts have been largely restricted to the development of mutant mice.

SUMMARY OF THE INVENTION

The present invention is the generation of a mouse strain with null mutations in the IFN regulatory gene, IRF-1. These mutant strains of mice are ideal models for the analyses of the expression of these transcriptional factors, IFNs and other genes that are affected by these genes. As well, the inducibility of IFNs, IRF-1 and IRF-2 genes after administration of IFNs or infection by viruses or other treatments establish the usefulness of these mice as animal models to study the roles of IFNs in development. Further, these animals provide relevant systems to test the influence of IFNs in rejection of tumors and pathogen infections as well as in autoimmune disease development.

BRIEF DESCRIPTION OF THE DRAWINGS

FIG. 8 shows Northern blots where priming with IFN-$\beta$ restores the response to poly(I):poly(C) in IRF-1 deficient cells. Embryonic fibroblasts were primed with (+) or without (−) IFN-$\beta$ (1000 IU/ml) 4 hours prior to induction by poly(I):poly(C) (100 μg/ml) and total RNA was prepared at the time indicated in the figure. Five micrograms was used for Northern blot analysis.

FIGS. 10A–10F shows graphic comparisons of levels of type I IFN mRNA at peak time. Type I IFN mRNA levels were quantitated by densitometer at the peak time (8 hours in Exp.1 and 12 hours in Exp.2 and Exp.3 after infection with NDV) and normalized by $\beta$-actin mRNA.

FIGS. 11A–11F are a graphic representations of quantitative Northern blot analysis of the time course of IFN-inducible genes' mRNA. mRNA was quantitated as described for FIG. 10 in experiment 1 (EXP.1) and experiment 2 (EXP.2)

FIGS. 13A–13F shows flow cytometric analysis of T cell subsets in IRF-1 deficient mice. Single cell suspensions were prepared from peripheral blood, spleen, and lymph nodes from 3-week-old littermate mice and stained with anti-CD4-PE and anti-CD8-FITC. Lymphocytes were gated as in FIG. 12 and 5000 cells were analyzed. The percentage of cells in relevant quadrants are indicated on the figure.

FIGS. 14A–14F shows fluorescence cell activator staining (FACS) analysis of T cell subsets in thymus. Thymocytes from the animals of FIGS. 13A–13F were stained with anti-CD4-PE and anti-CD8-FITC. In the lower four panels, CD4$^-$8$^+$ T cells were enriched from thymocyte populations by eliminating CD4-positive T cells. After depletion, cells were stained with anti-$\alpha\beta$TcR monoclonal antibodies-PE or anti-$\gamma\delta$TcR monoclonal antibodies-PE, and with anti-CD8-FITC. CD4$^-$8$^+$ T cell-enrichment experiments were done three times and one representative set of data is shown.

DESCRIPTION OF THE PREFERRED EMBODIMENTS

In preparation for in vitro and in vivo studies of the role of type I interferons in normal and disease situations, animals that contain mutations in the genes of IRF-1 were generated. The animal species used was mouse since mice have become the preferred animal for use in disease studies as the mouse immune system closely resembles that of the human. The strategy for obtaining mice having mutated IRF-1 genes involved manipulation of the genes of the transcriptional factors rather than the genes of the interferons themselves. One reason for taking this approach was that there are multiple copies of the type I interferon genes, which obviously make it difficult to create mutations in all of them (Stewart, 1979; Weissman and Weber, 1986; Pestka et al., 1987; Vilcek, 1990). For another reason, this approach allows for the dissection of the functions of each of the two interferon response factors. Following this strategy mutant mouse strains carrying null mutations of the gene of IRF-1 were created.

Targeting the IRF-1 Gene and Generation of Mutant Mice

Figure 1:
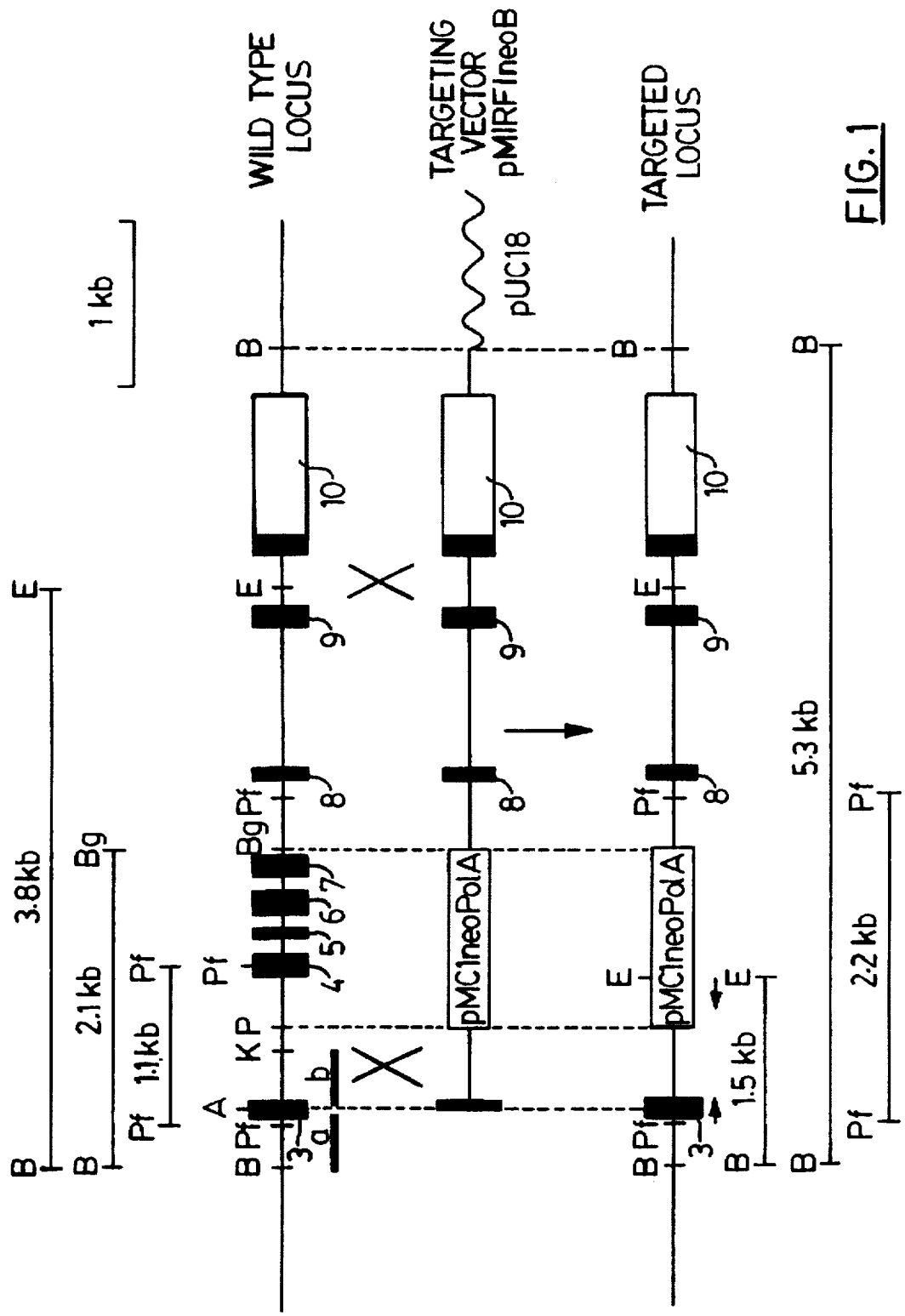
FIG. 1 is a schematic diagram of the targeting strategy of the IRF-1 gene. B, Pf, K, P, Bg, and E represents restriction enzyme sites for BamHI, PflMI, KpnI, PstI, Bgl II and EcoRI, respectively. Black boxes indicate coding exons. A 1.2 kb PstI-Bgl II fragment from the IRF-1 gene was deleted and replaced with a neo gene (the intron 7 Bgl II site is eliminated in the targeted locus). Arrows indicate the positions and directions of the IRF-1 flanking primer and neo primer used for PCR screening. IRF-1 probes used for genomic Southern blot analysis are shown as black bars, designated with a and b.
Figure 2:
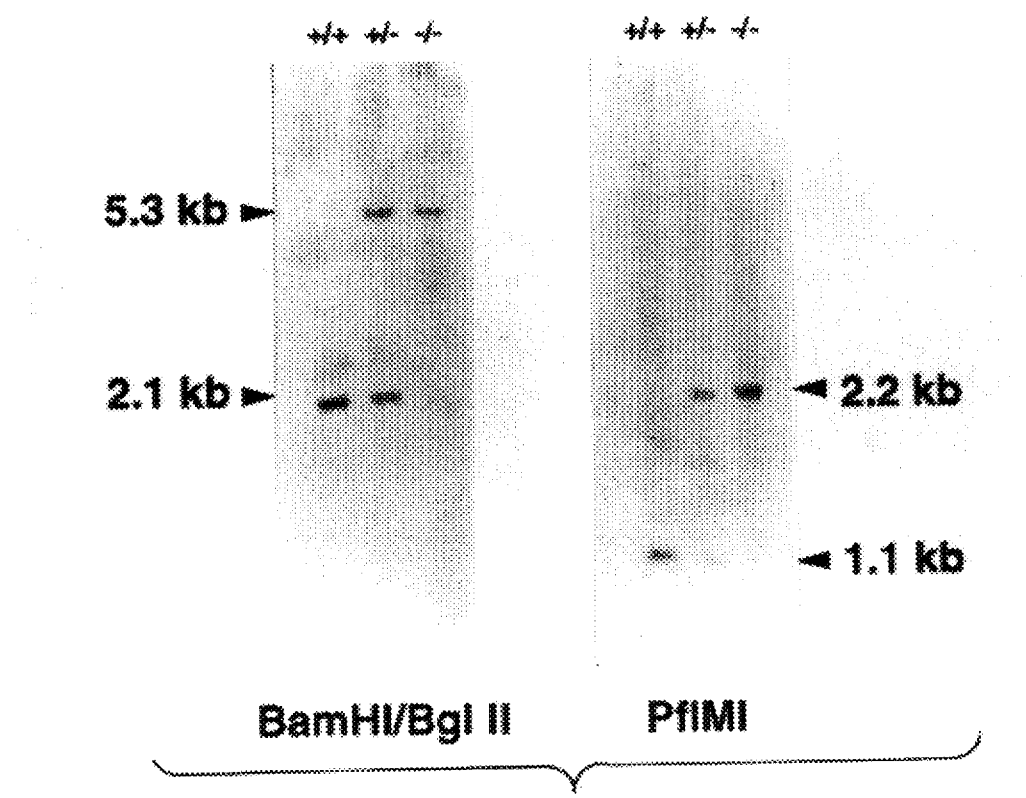
FIG. 2 shows Southern blot analysis of tail DNAs. Tail DNAs were digested with BamHI and Bgl II, probed with a, or digested with PflMI and probed with b.

The IRF gene family shares a highly conserved amino acid sequence in the N-terminal end (Miyamoto et al., 1988; Harada et al., 1989; Driggers et al, 1990; Veals et al., 1992). This N-terminal domain is attributed to the DNA binding specificity of IRF-1 as demonstrated by an analysis of a series of IRF-1 deletion mutants; without this domain, DNA binding is abrogated completely (Uegaki et al., 1993; M. Miyamoto, H. Harada, T. T., unpublished results). The construct used for targeted disruption of the IRF-1 gene, pMIRF-1neoB, contains 4.9 kb of homologous IRF-1 genomic DNA, and a deletion of 1.2 kb into which the neomycin resistance gene has been introduced in the same transcriptional orientation as IRF-1 (FIG. 1). This deletion (a.a. 63–223) removes exons which encode the critical part of the DNA binding domain and inactivates IRF-1 by loss of DNA binding activity.

pMIRF1neoB was introduced into $5 \times 10^7$ D3 ES cells by electroporation (Doetschman et al., 1985). G418 resistant colonies were analyzed for the homologous recombination event between the construct and the endogenous IRF-1 gene by polymerase chain reaction (PCR). Targeted clones obtained by PCR screenings were confirmed by genomic Southern blot analysis. The average frequency of homologous recombination was about 1 in $10^7$ ES cells or 1 in 150 G418-resistant colonies. Six clones were chosen for injection into blastocysts to generate chimeric mice and three clones gave rise to germline transmission. Homozygous mice were generated by intercross of heterozygous mice and the mutated IRF-1 gene was confirmed by genomic Southern blot analysis of tail DNA (FIG. 2).

Mutant IRF-1 heterozygous and homozygous mice showed no difference in size, behaviour and reproductive ability, as compared to wild type littermates and appeared to have healthy life spans (observed up to 60 weeks). Gross examination of internal organs also showed no abnormality in these mutant mice.

Figure 3:
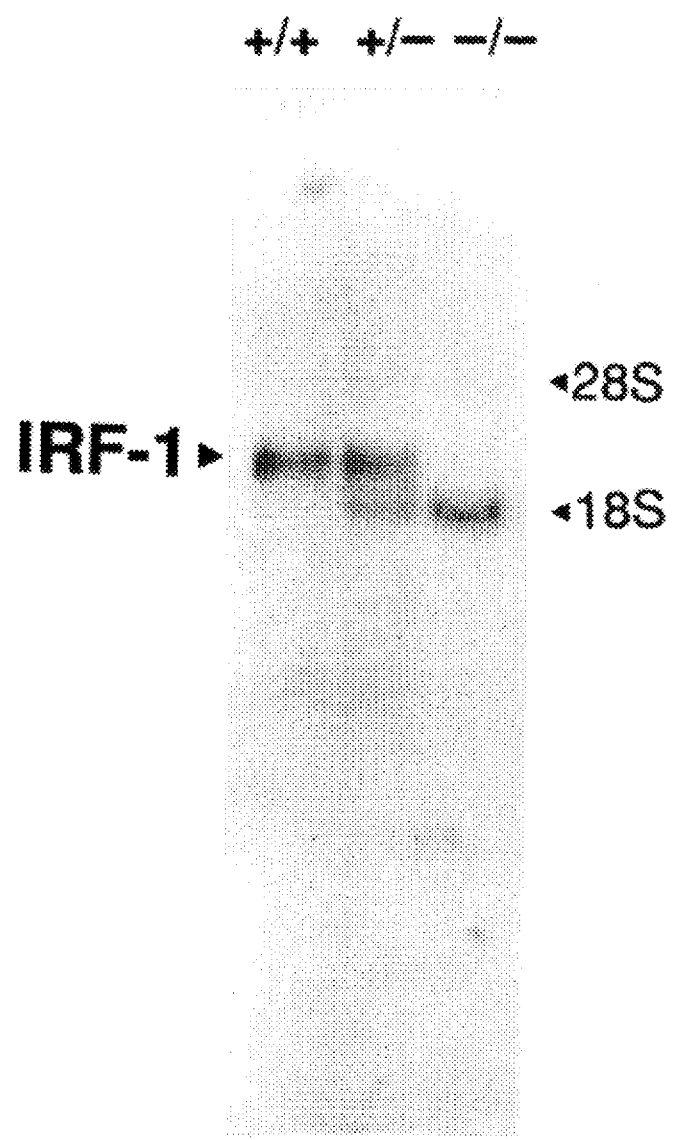
FIG. 3 shows Northern blot analysis of IRF-1 expression in splenocytes. Splenocytes were singly suspended, and stimulated with IFN-$\beta$ (2000 IU/ml; Lee Biochemical) for 3 hours. Five micrograms of total RNAs was subjected to Northern blot analysis.
Figure 4:
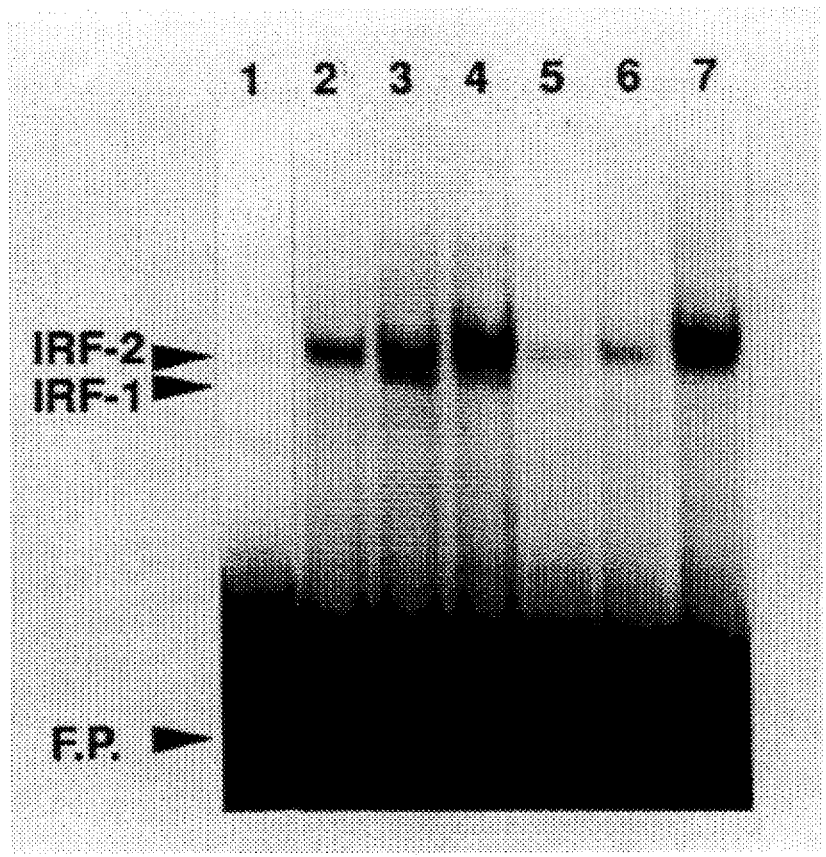
FIG. 4 shows gel shift analysis of IRF-1. Whole-cell extract were prepared from mock-induced (lane 2,5), IFN-$\beta$-treated (lane 3,6), or NDV-infected (lane 4,7) embryonic fibroblasts derived from IRF-1 heterozygous mutant (lane 2–4) or IRF-1 homozygous mutant (5–7) embryos. Gel-shift analysis was carried out using 5 fmol of $^{32}$P-labelled C7 oligomer (Fujita et al., 1987) as the probe, with (lane 2–7) or without (lane 1) 10 μg of whole-cell extract. The arrowheads indicate the factor-DNA complex. F.P. indicates free probe.

To determine that the expression of IRF-1 was absent in IRF-1 mutant mice, total RNA from splenocytes was isolated. Because the constitutive level of IRF-1 expression is low, cells were treated with IFN-β to induce IRF-1 before preparing total RNA. As expected, the full length IRF-1 mRNA was absent in homozygous mice; however, a shorter transcript was observed (FIG. 3). To confirm that no functional IRF-1 protein was produced in homozygous mice, total cellular extract was prepared from embryonic fibroblasts after either NDV infection or stimulation of IFN-β, and analyzed by a gel shift assay. Shifted bands corresponding to IRF-1 were detectable in IRF-1 heterozygous cells but not in IRF-1 deficient cells; whereas, IRF-2 binding activity was seen in both types of cells (FIG. 4). Furthermore, there was no rapidly migrating band which might represent a truncated form of IRF-1. Collectively, these results indicate that IRF-1 has been functionally inactivated in the mutant mouse of the invention.

IRF-1 is Differentially Required for the Induction of Type-I IFN Genes

To determine whether induction of type I IFN genes is affected by the absence of IRF-1, embryonic fibroblasts were exposed to either poly(I):poly(C) or NDV. IRF-1 expression is inducible by both agents and follows the same kinetics as the induction of type I IFN genes in embryonic fibroblasts (data not shown).

Figure 5:
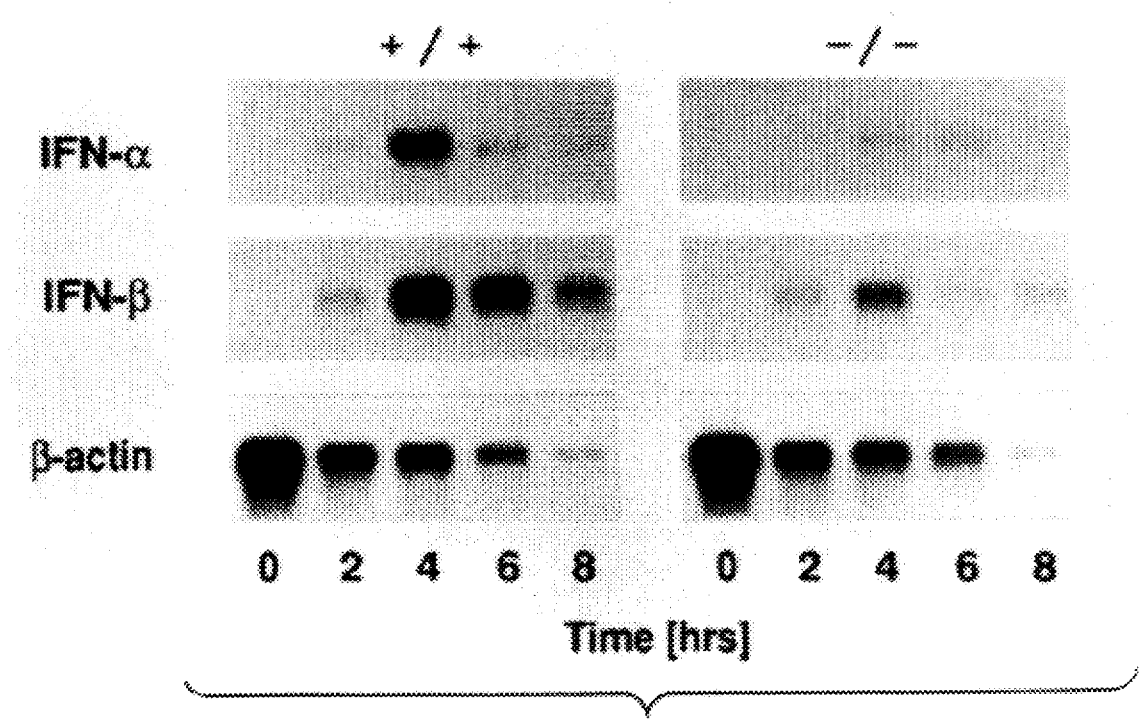
FIG. 5 shows Northern blots of the time course of poly(I):poly(C) induction of type I IFN mRNAs in embryonic fibroblasts derived from littermate embryos. Embryonic fibroblasts derived from IRF-1 wild type (+/+) and homozygous mutant embryos (−/−) were induced with 100 μg/ml of poly(I):poly(C) (Yamasa Shoyu) in the presence of DEAE dextran (500 μg/ml). Total RNAs were extracted at the time indicated in the figure and five micrograms was used for Northern blot analysis.
Figure 6:
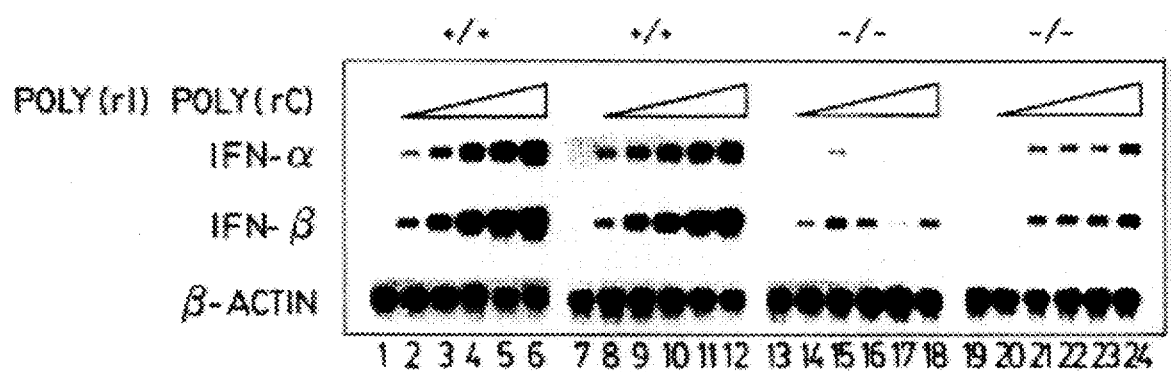
FIG. 6 shows Northern blots of the dose response to poly(I):poly(C) for induction of IFN mRNA. Cells were derived from IRF-1 wild type (1–12), and IRF-1 homozygous mutant (13–24) littermate embryos. Cells were induced with 0 (1,7,13,19), 3 (2,8,14,20), 10 (3,9,15,21), 30 (4,10, 16,22), 100 (5,11,17,23), 300 (6,12,18,24) μg/ml of poly(I):poly(C). Total RNAs were extracted at 4 hours after induction and five micrograms were used for Northern blot analysis.
Figure 7A:
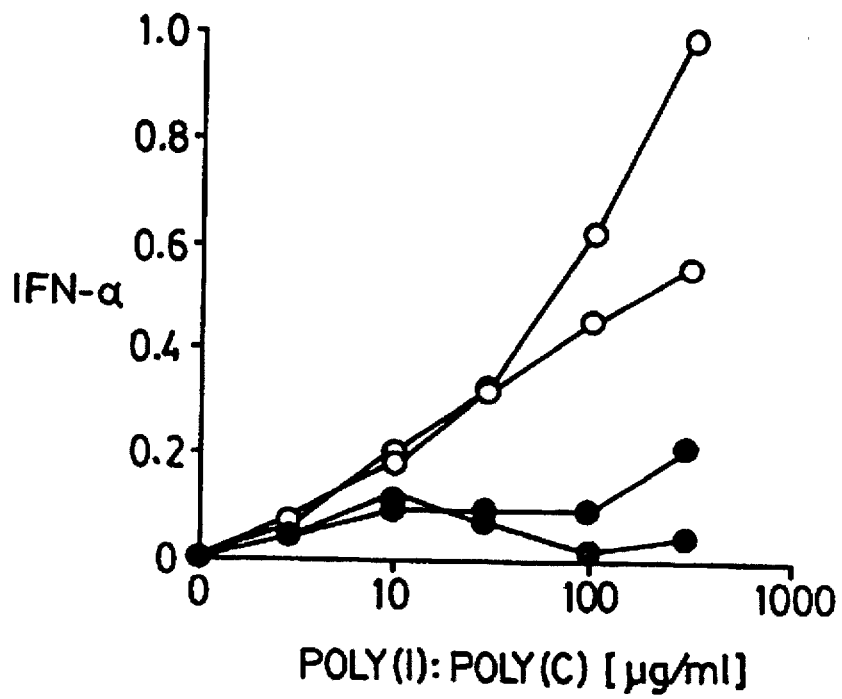
FIGS. 7A–7B shows plots of the results shown in FIG. 7. Type I mRNA levels was quantitated by an imaging analyzer (BAS 2000, Fuji) and relative amount of mRNAs normalized by $\beta$-actin mRNA are depicted in the figure. Wild type cells (o—o), IRF-1 deficient cells (●—●).
Figure 7B:
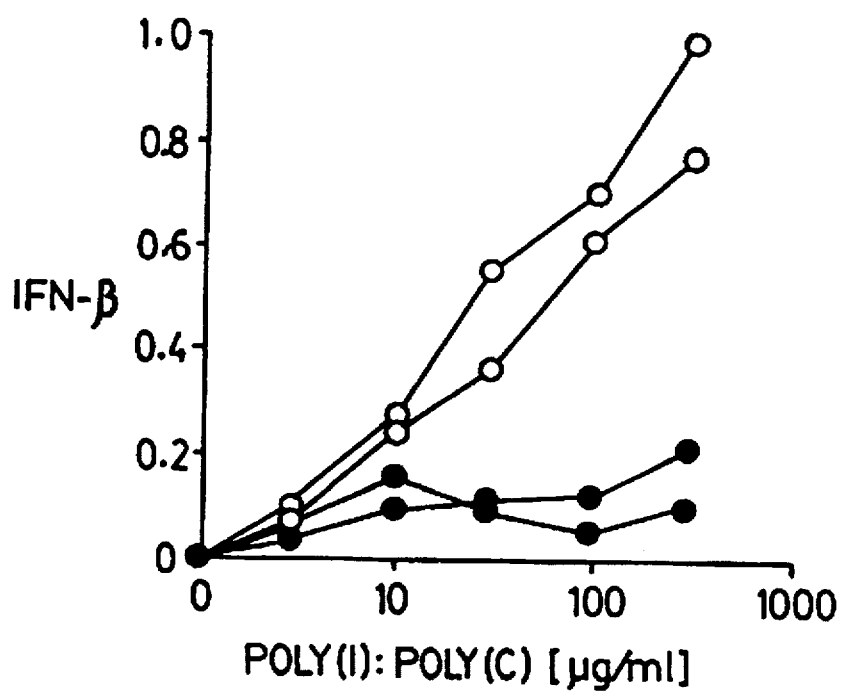

Total RNA was isolated from embryonic fibroblasts induced by poly(I):poly(C), and mRNA levels were examined by Northern blot analysis. In IRF-1 deficient fibroblasts, type I IFN mRNAs were inducible and peaked at 4 hours after induction as seen in wild type cells (FIG. 5). However, mRNAS levels were dramatically reduced (3 to 10-fold) in IRF-1 deficient fibroblasts, indicating that IRF-1 is essential for optimal induction of type I IFN by poly(I):poly(C). The dose response of cells to poly(I):poly(C) was also examined. IRF-1 deficient cells are refractory to increased amounts of poly(I):poly(C) whereas wild type cells induce type I IFN in a dose dependent manner (FIG. 6 and FIGS. 7A–7B).

Figure 9:
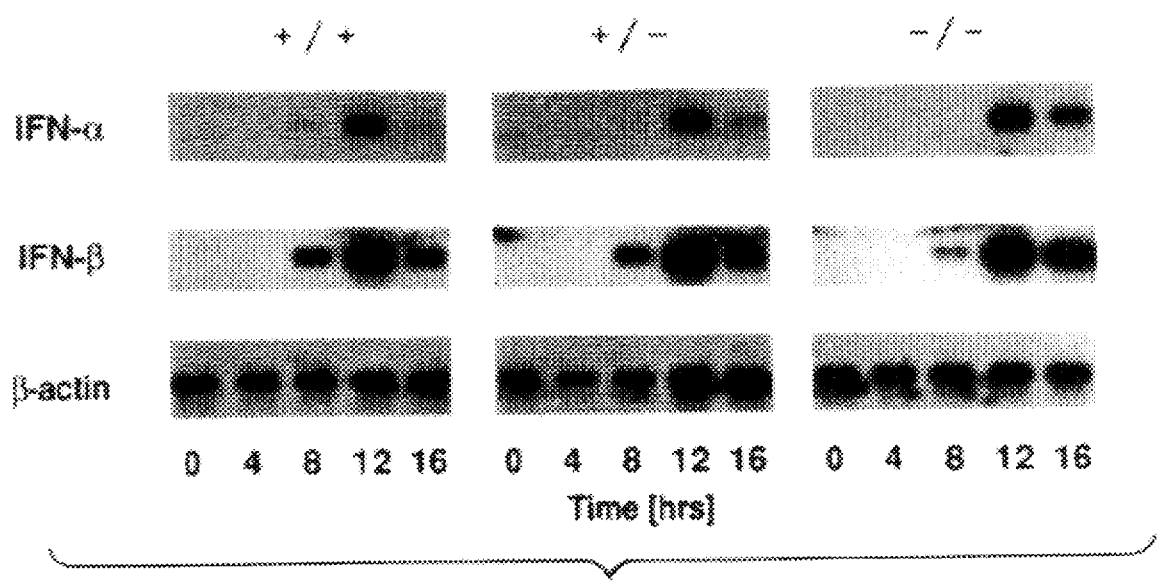
FIG. 9 shows Northern blots of the time course of NDV induction of type I IFN mRNAs in embryonic fibroblasts. Cells were derived from IRF-1 wild type (+/+), heterozygous mutant (+/−), and homozygous mutant (−/−) littermate embryos. Total RNAs were extracted at the time indicated in the figure and five micrograms was used for Northern blot analysis.

Next, embryonic fibroblasts were infected with NDV and the time course of type I IFN induction was analyzed by Northern blot up to 16 hours after infection. Stimulation with NDV led to the higher levels of type I IFN than those induced by poly(I):poly(C) and the gene induction peaked at 8–12 hours after infection (FIG. 9). Surprisingly, type I IFN could be induced in homozygous mutant cells to similar levels as those of wild type and heterozygous cells. Similar results were obtained in three independent experiments when the mRNA levels were compared at the peak of the induction (FIGS. 10A–10F). Peritoneal macrophages for the induction of type I IFN after NDV infection were also examined. Type I IFNs of IRF-1 deficient macrophages were also induced to similar levels as those of wild type and heterozygous cells (data not shown).

Treatment of cells with type I IFN prior to stimulation with poly(I):poly(C) results in superinduction of type I IFN expression, a phenomenon known as priming (Stewart II et al., 1971; Stewart II, 1979). Interestingly, priming restored the induction in IRF-1 deficient cells to levels similar to wild type cells (FIG. 8). As IFN-β treatment alone cannot activate the expression of type I IFN genes, IFN-β may induce certain compensatory pathways that can be activated by poly(I):poly(C). In summary, the results demonstrate that IRF-1 is differentially required for the transcriptional activation of type I IFN genes and suggest the existence of at least one alternative IRF-1 independent mechanism.

IFN-inducible Genes are not Affected by the Absence of IRF-1

IRF-1 has also been implicated in the stimulation of IFN-inducible genes by type I IFN (Harada et al., 1990; Reis et al., 1992; Au et al., 1992). The expression of several IFN-inducible genes in IRF-1 deficient embryonic fibroblasts was examined. The kinetics of induction from 1 to 24 hours after stimulation of IFN-β was examined by Northern blot analysis, and there was no detectable difference between wild type and IRF-1 deficient cells in both the basal level of expression and inducibility of all the genes examined, including 2'-5'OAS, p65 double-stranded RNA dependent protein kinase (PKR), 1–8, and H-2K$^b$ (FIGS. 11A–11F).

Dramatically Reduced Level of TcRαβCD4$^-$8$^+$ T Cells in Homozygous Mutant Mice IRF-1 deficient mice have been kept free of specific mouse pathogens. Under these conditions, the mutant mice were healthy, and there was no significant difference between littermates in the total number of cells in peripheral blood, spleen, lymph nodes, and thymus.

The IRF-1 gene is induced by various cytokines which affect the development of haematopoietic cells (Miyamoto et al., 1988; Fujita et al., 1989c; Pine et al., 1990; Abdollahi et al., 1991). In immunoglobulin-enhancer-driven IRF-1 transgenic mice, the mature B cell population is strikingly reduced, and the bone marrow might be involved (Yamada et al, 1991). In addition, an IRF-1 binding motif was found within the promoter of the IL-7 receptor gene (Pleiman et al., 1991) and IL-7 has been known as pre-B cell growth factor (Namen et al., 1988). To determine whether the B cell lineage is affected by the absence of IRF-1, the surface expression of B cell markers, B220 (CD45) and IgM, was examined by fluorescence-activated cell sorting (FACS). Results indicated that in IRF-1 deficient mice the B cell population was not affected in peripheral blood, spleen, lymph nodes, bone marrow and peritoneal exudate cells (data not shown).

Figure 12:
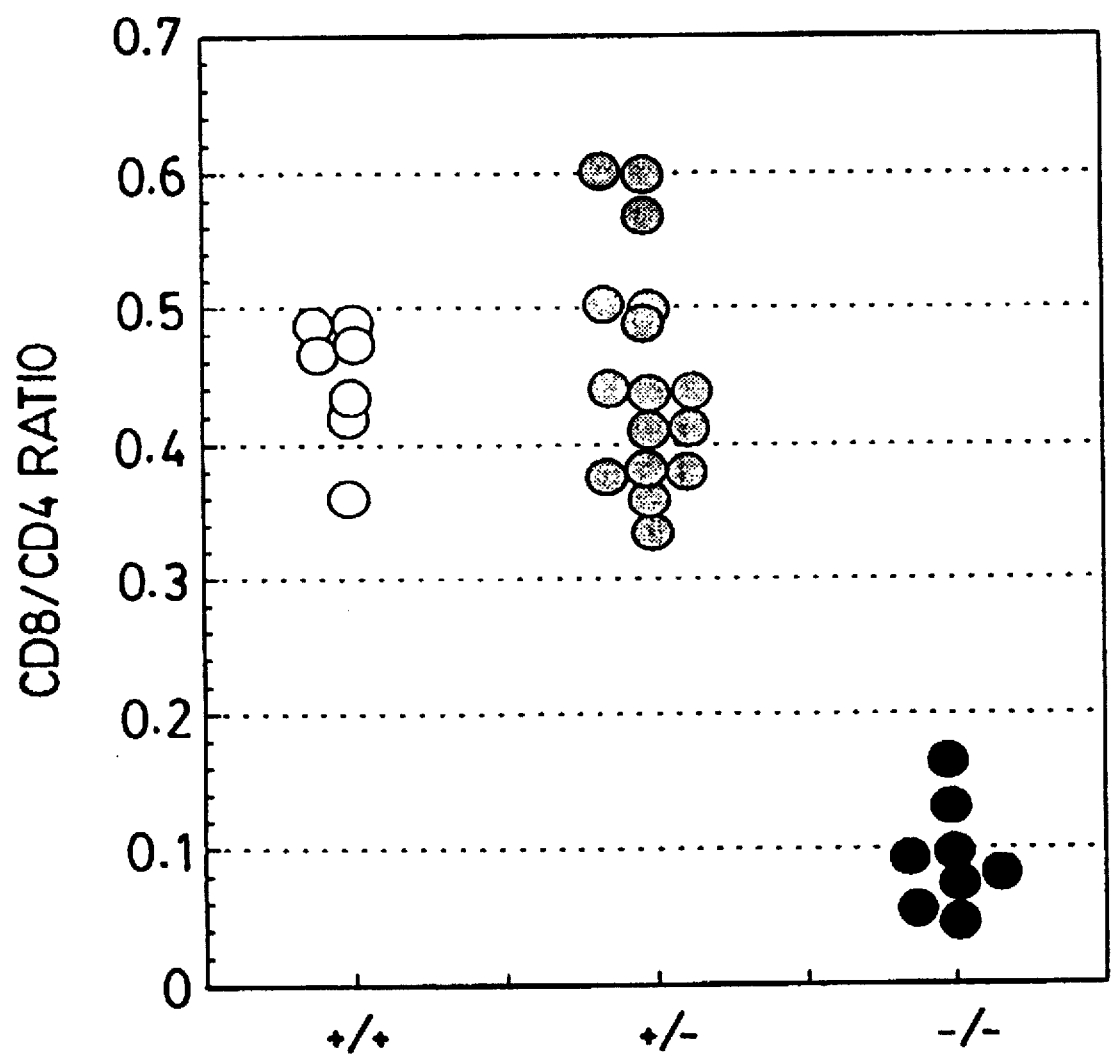
FIG. 12 shows CD4$^+$/CD8$^+$ T cell ratio in peripheral blood. Data represent 5 littermate groups generated by intercross of heterozygous mice with H-2b haplotype. The animals ranged between 6 to 10 weeks of age. Single cell suspensions were stained with anti-CD4-phycoerythin (PE) and anti-CD8-FITC. Lymphocytes were gated based on the forward and sideways light scattering properties, and 10000 cells were analyzed.

Surface expression of other immunological markers was also studied. A series of antibodies used against T cell markers were L3T4 (CD4), Ly-2 (CD8α), Ly-3 (CD8β), CD3 ε, TcRαβ, TcRγδ, Thy-1.2, Ly-1 (CD5), and Pgp-1 (CD44). Monoclonal antibodies Gr-1 and Mac-1 were used for non-lymphoid cell stainings. These studies showed that IRF-1 deficient mice had immune cells with normal number and distribution except for a $CD4^-8^+$ T cells. In fact, a dramatic reduction of $CD4^-8^+$ T cells (10-fold) was evident in peripheral blood (FIGS. 12 and 13A–13B), spleen, lymph nodes (FIGS. 13C–13D and 13E–13F respectively), and thymus (FIGS. 14A–14B). Staining with antibodies against Ly-2 and Ly-3 showed the same result (staining data with anti-Ly-3 not shown). On the other hand, $CD4^+8^-$ T cells were often, but not always, increased in number in mutant mice, which appears to compensate the decreased numbers of $CD4^-8^+$ T cells as is seen in the case of $CD8^+$ T cell deficient mice (Fung-Leung et al., 1991).

The number of $CD4^+8^+$ T cells in the thymi of homozygous mutant mice appeared to be normal or slightly elevated (FIGS. 14A–14B). To further examine the mechanisms of reduced number of $CD4^-8^+$ T cells, thymic subsets were analyzed after $CD4^+$ T cell depletion with an anti-CD4 antibody and complement in vitro. After $CD4^+$ T cell depletion, the number of mature $TcRαβ^+CD4^-8^+$ T cells in the thymi of IRF-1 deficient mice was found correspondingly decreased (FIGS. 14C–14D). Similar results were obtained after in vivo treatment with dexamethasone which selectively depletes $TcRαβ^+CD4^-8^+$ T cells (Scollay et al., 1984) (data not shown). In addition, $TcRαβ^-CD4^-8^+$ thymocytes, which are thought to represent an intermediate between $CD4^-8^-$ and $CD4^+8^+$ T cells, were present in normal numbers (FIGS. 14C–14D). These data indicate that IRF-1 deficient mice have a thymocyte developmental defect between the double positive and the single positive stage during $CD8^+$ T cell ontogeny.

The number of $TcRγδ^+CD4^-8^-$ T cells was not affected in homozygous mutant mice (FIGS. 14E–14F).

We also examined the level of CD8 (Ly-2) expression on both immature and mature thymocytes by determining the mean levels of fluorescent staining intensity; however, there was no difference between wild type mice and IRF-1 deficient mice (data not shown).

Figure 15:
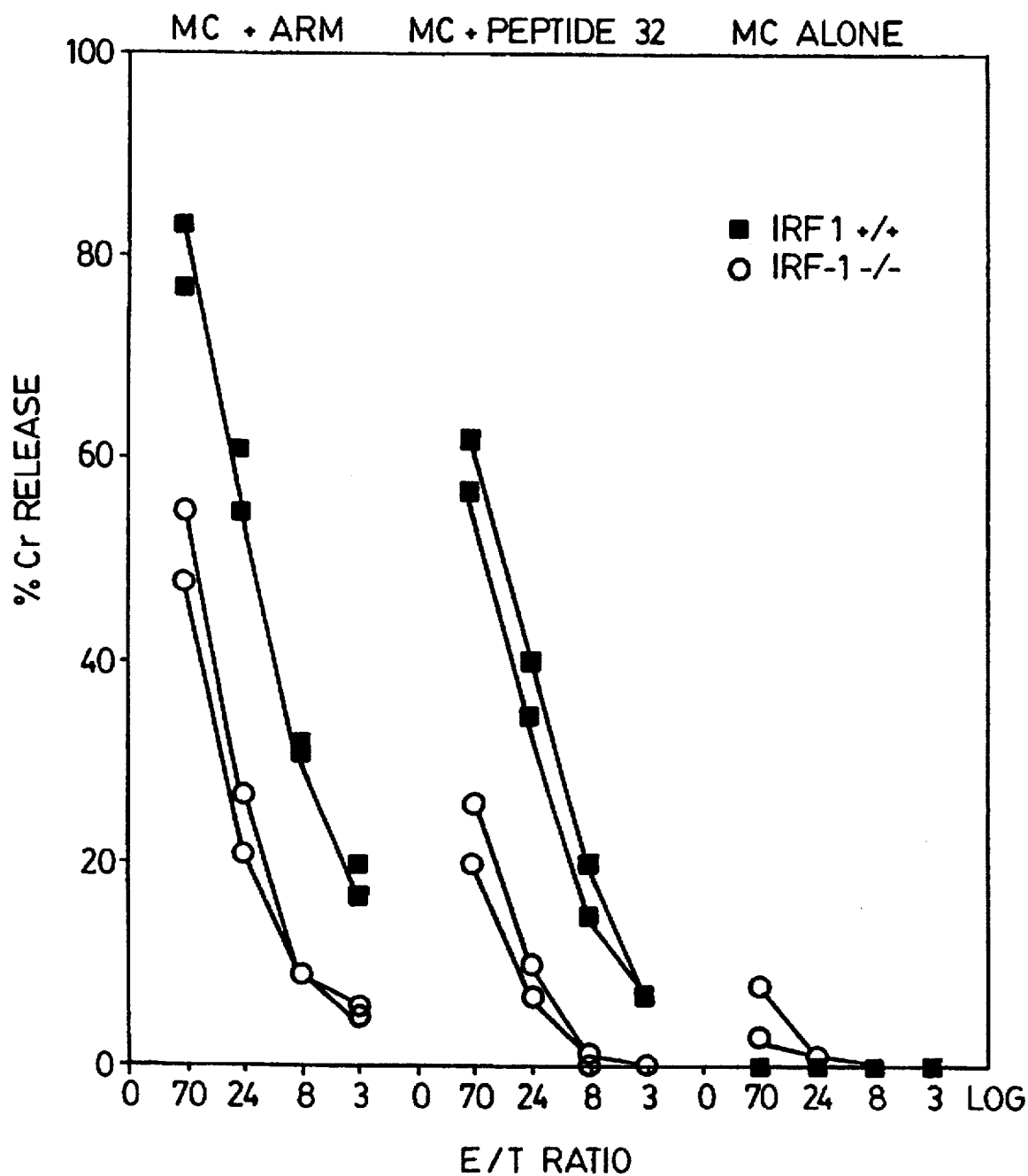
FIG. 15 are graphs showing reduced CTL activity against LCMV in IRF-1 deficient mice. Four mice were intravenously infected with 200 pfu of LCMV (Armstrong strain), and sacrificed 8 days after infection. CTL activity was assayed by $^{51}$Cr release from target cells, which are LCMV-infected (MC+Arm), LCMV-peptides loaded (MC+peptide 32), or mock-infected (MC alone) MC57G fibrosarcoma cells.
Figure 17:
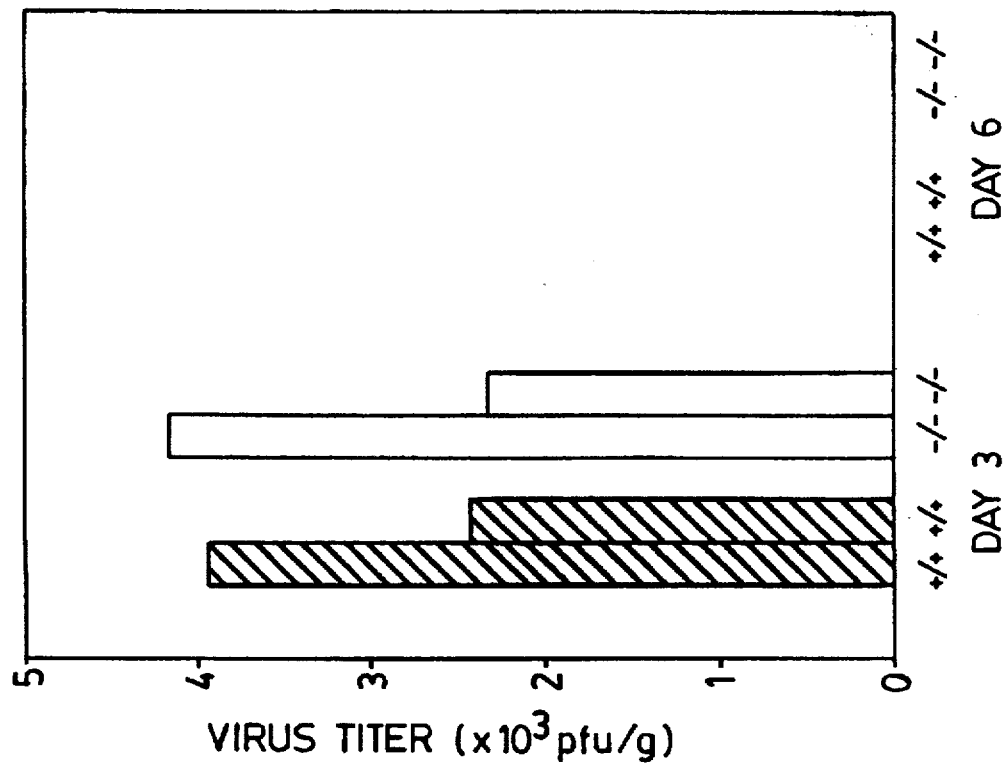
FIG. 17 is a graph of the LCMV clearance in IRF-1 deficient mice. LCMV titer was measured in spleen by the plaque-forming assay (Battegay et al., 1991) at the times indicated in the figure.
Figure 16:
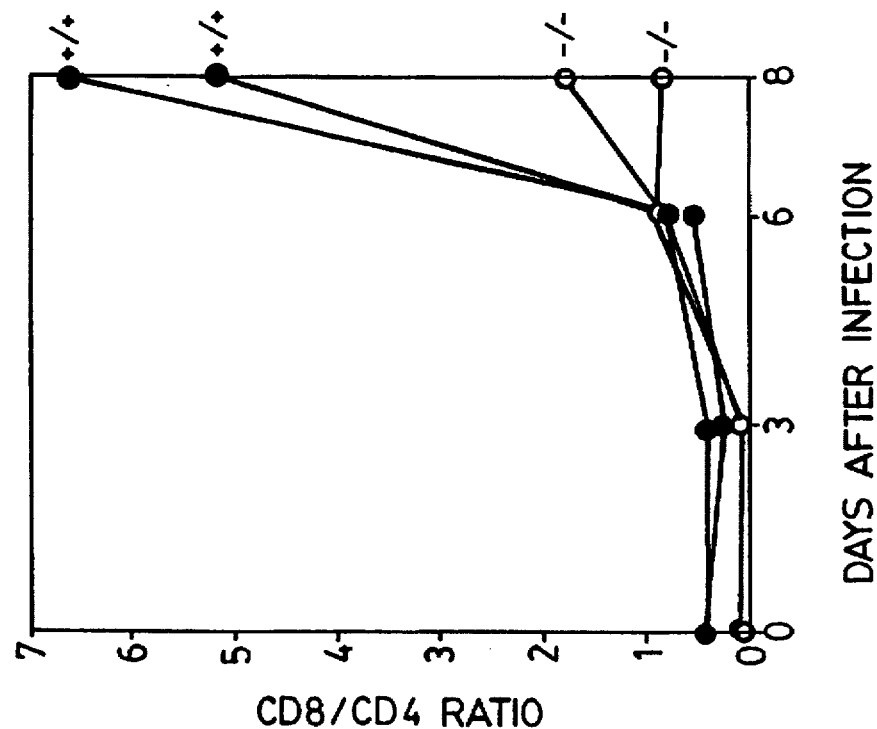
FIG. 16 is a graph of the time course of CD8$^+$/CD4$^+$ T cell ratios after infection. CD8$^+$/CD4$^+$ T cell ratio was measured as in FIG. 15.
Figure 18A:
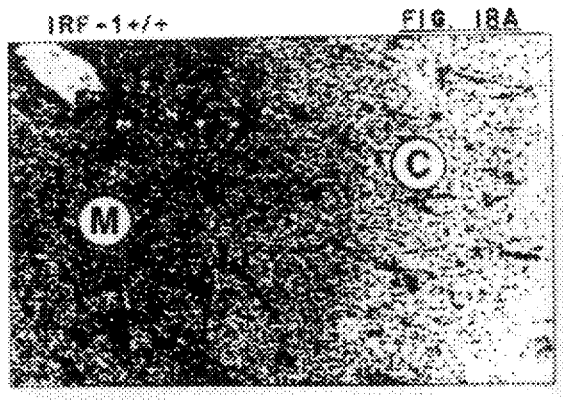
FIGS. 18A–18B shows immunohistochemistry of thymic sections from IRF-1 deficient mice. Frozen sections of thymi from wild type (+/+) and mutant (−/−) mice were sequentially treated with anti-mouse MHC class I (M1/42.3.9.8.HLK) supernatant, and horseradish peroxidase conjugated-anti-rat IgG (Sigma), and peroxidase staining. Medullary (M) and cortical (C) areas are indicated. (x100).
Figure 18B:
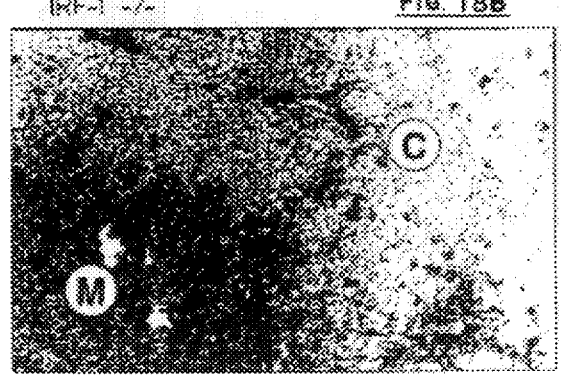
Figure 19A:
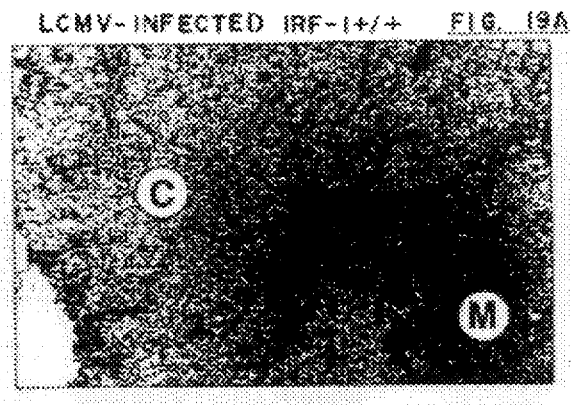
FIGS. 19A–19B shows immunohistological staining of thymi from mice infected with LCMV. Thymi were removed from mice on day 8 after infection and stained as above.
Figure 19B:
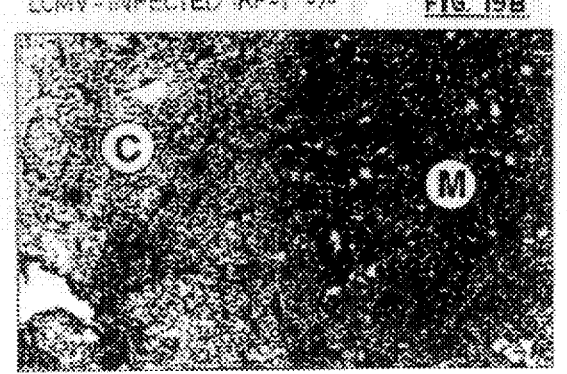

Cytotoxic Activities of T cells against LCMV $CD8^+$ T cells in mice have cytotoxic effector functions. Cytotoxic T cells require functional antigen-MHC class I complex both for development and effector functions. To address whether T cells from IRF-1 deficient mice are able to mount an effective cytotoxic response against virus, mice were infected with lymphocyte choriomeningitis virus (LCMV). In homozygous mutant mice, cytotoxic responses against LCMV-infected target cells were significantly reduced (FIG. 15). This finding may simply reflect the decreased number of cytotoxic precursor cells in the spleen, since some cytotoxic activity against virus infected cells was detected in IRF-1 deficient mice. In fact, the $CD8^+/CD4^+$ T cell ratio remained below that of wild type mice throughout the course of LCMV infection, which is known to induce peripheral expansion of $CD8^+$ T cells (FIG. 16) (Zinkernagel and Hengartner, 1992). Most importantly, viral titers from LCMV-infected mutant mice 3 days after infection were similar to that of wild type mice and the virus was cleared 6 days after infection from all strains tested (FIG. 17), implying that $CD8^+$ T cells in IRF-1 deficient mice are functional and have cytotoxic activity against the virus infected cells in vivo.

TABLE 1

Anti-VSV neutralizing antibody in IRF-1 deficient mice
Titer of neutralizing antibody $(\log_2 \times 10^{-1})^a$

| IRF-1 | day4 | | day8 | | day16 | |
|---|---|---|---|---|---|---|
| | IgM | IgG | IgM | IgG | IgM | IgG |
| +/+ | 8 | 0 | 4 | 6 | 0 | 10 |
| +/+ | 8 | 0 | 4 | 6 | 1 | 9 |
| +/+ | 8 | 0 | 4 | 7 | 0 | 10 |
| +/+ | 9 | 0 | 3 | 7 | —[b] | — |
| +/+ | 8 | 0 | 3 | 7 | — | — |
| –/– | 8 | 0 | 4 | 6 | 0 | 10 |
| –/– | 8 | 0 | 4 | 6 | 1 | 10 |
| –/– | 8 | 0 | 3 | 8 | 0 | 9 |
| –/– | 8 | 0 | — | — | — | — |
| –/– | 7 | 0 | — | — | — | — |

Table Footnotes
Table 1. Neutralizing antibodies against VSV in IRF-1 deficient mice.
Mice were injected intravenously with VSV ($2 \times 10^6$ pfu).
[a]Neutralizing antibodies titers represent 2-fold dilution factor starting at 1:40.
[b]Not determined because mice had died.

Humoral Response to Vesicular Stomatitis Virus (VSV)

Next, mice were challenged with vesicular stomatitis virus (VSV) which can induce strong humoral response in normal mice (Fung-Leung et al., 1991). In normal mice, anti-VSV IgM neutralizing antibodies appeared on day 4 after infection and were switched to IgG neutralizing antibodies by day 8 after infection (Table 1). The kinetics of immunoglobulin-class-switching and the levels of antibodies were comparable between wild type and IRF-1 deficient mice. Since, immunoglobulin-class-switching after VSV infection is strictly dependent on $CD4^+$ helper T cells (Gupta et al., 1986), these data show that immunoglobulin production and $CD4^+$ helper T cells activities are normal in IRF-1 deficient mice.

MHC Class I Expression in IRF-1 Mutant Mice

MHC class I expression has been shown to be indispensable for the development of $TcRαβ^+CD4^-8^+$ T cells. Mice lacking $β_2$ microglobulin have no or few $TcRαβ^+CD4^-8^+$ T cells (Zijlstra et al., 1990, Koller et al., 1990; Chan et al., 1993) and mice lacking TAP-1, a protein transporter involved in MHC class I antigen presentation, show a 30- to 40-fold reduction of $TcRαβCD4^-8^+$ T cells (Kaer et al, 1992). In addition, MHC class I gene promoters contain the IRF-1 binding motif (Korber et al., 1988; Miyamoto et al., 1988; Tanaka et al., 1993) and MHC class I promoters can respond to IRF-1 (Harada et al.,1990), such that IRF-1 alone is sufficient to transactivate both transfected and endogenous MHC class I genes (Chang et al., 1992). Taken together, it was conceivable that IRF-1 deficient mice had some defect in the expression of MHC class I in the thymus, causing a weaker interaction with precursors of class I-restricted T cells during positive selection, and thus, resulting in a decreased number of peripheral CD4⁻8⁺ T cells.

To examine this possibility, the MHC class I expression in the thymus was measured by immunohistochemical analysis. However, anti-H2 monoclonal antibodies, M1/42.3.9.8.HLK and B8-24-3, produced typical confluent staining pattern in the medulla, and faint reticular staining pattern in the cortex in both wild type and IRF-1 mutant mice, and no significant differences were seen between these strains. Since MHC class I expression is inducible in cortical lymphocytes and epithelial reticular cells (David-Watine et al, 1990), the induction of MHC class I expression in cortical areas after LCMV infection was examined. Thymi from both types of mice exhibited comparable strong reticular staining patterns of MHC class I in the cortex, further indicating the notion that the block of CD8⁺T cell development is independent of MHC class I /TcR interactions.

Discussion
IRF-1 and IFN Systems

Several lines of evidences suggest that IRF-1 is a critical transcriptional activator of type I IFN. First, mutations within the promoter of the IFN-β gene have revealed the necessity of IRF-1 binding elements (IRF-Es) for full transcriptional activation (Fujita et al.,1987; Fujita et al.,1988). Further, IRF-Es alone can mediate the response to virus stimulation (Fujita et al.,1987; Naf et al.,1991). Second, transfection of an IRF-1 expression plasmid can activate endogenous and exogenous IFN-α and IFN-β genes (Fujita et al., 1989b; Harada et al.,1990; Palombella and Maniatis, 1992). Finally, induction of the IFN-β gene is dramatically reduced in GM-637 cells when antisense IRF-1 is expressed (Reis et al.,1992). Utilizing mice of the invention lacking IRF-1 expression through homologous recombination in embryonic stem cells, the role of IRF-1 in type I IFN induction was examined. The levels of IFN induction were studied by using two inducers, poly(I):poly(C) and NDV, which have been recognised as potent inducers of type I IFN, possibly via a common pathway triggered by double stranded RNA structure (reviewed by Vilcek, 1990). The results suggest that the mechanisms of type I IFN gene induction may differ between the two inducers. In fact, the induction of type I IFN genes was markedly reduced in IRF-1 deficient cells when cells were treated by poly(I):poly (C). In contrast, the level of induction remained essentially the same as that of wild type upon NDV infection. Hence, the results may indicate the existence of an IRF-1 dependent pathway and an IRF-1 independent pathway for type I IFN induction. The signal for type I IFN induction by poly(I) :poly(C) is primarily mediated by IRF-1, while additional signal cascades might be involved in NDV infection.

The existence of an alternative pathway is also supported by the observation that type I IFN induction by poly(I):poly (C) in IRF-1 deficient cells is restored by priming with IFN-β. Although it is not clear whether this pathway is the same as that of NDV infection, it appears likely that synthesis of a factor, which can compensate for the absence of IRF-1, is induced in IFN-primed and NDV-infected cells. In fact, when embryonic fibroblasts were induced by NDV in the presence of cycloheximide, the IFN-β mRNA levels dropped by 5-fold in both wild type and mutant cells, supporting the view that the conjectured factor also needs to be synthesized de novo after viral induction for maximal gene expression. Since IFN-β alone could not induce type I IFN induction, the factor induced by IFN-β needs to be modified through a signal elicited by the virus or poly(I) :poly(C). It has been previously proposed that in HeLa cells an IFN-inducible factor is required for induction of the IFN-β gene (Enoch et al., 1986). The results herein indicate that, in addition to IRF-1 which is itself IFN-inducible (Fujita et al.,1989c), yet another IFN-inducible factor can function in the type I IFN induction. Such a factor is also expected to be more active in the absence of IRF-1, a phenomenon reminiscent of myoD deficient mice in which another myogenic factor myf-5 is unusually up-regulated (Rudnicki et al., 1992)

At present, the nature of such factor or factors remains unclear. Besides IRF-1, several factors have been identified in the synergistic activation of type I IFN genes. Such factors include NF-κB, Oct-1 and CREB/ATF in the promoter of the IFN-β gene, and TG-factor in that of the IFN-αs genes (Fujita et al., 1989a; Lenardo et al., 1989; Visvanathan and Goodbourn, 1989; Leblanc et al., 1990; MacDonald et al., 1990; Du and Maniatis, 1992). Based on the analysis of mutations within the IRF binding sites of the IFN-β gene (Fujita et al., 1987; Fujita et al., 1988), it seems unlikely that these factors can completely substitute for IRF-1 but may contribute to the leaky activation seen upon poly(I):poly(C) induction. Thus, it is most likely that another factor that binds IRF-Es may be involved in the IRF-1 independent pathway. It is assumed that this pathway is not operative in some cell lines such as GM-637, in which inhibition of IRF-1 expression correlates with the inhibition of type I IFN gene induction (Reis et al., 1992).

There are several transcription factors known to belong to the IRF gene family. A transcription factor designated ICSBP was shown to bind the same target DNA element (Driggers et al., 1990). However, it has been reported that ICSBP may act as a negative regulatory factor of both IC8 and PRD-I (IRF-1 binding motif) containing promoters (Weisz et al., 1992). Recently, another member of the IRF gene family, I8GF-3γ, was cloned and shown to specifically bind to the promoters of various IFN genes (Veals et al., 1992). As ICSBP and ISGF-3γ do not appear to activate transcription of type I IFN genes, there are perhaps unidentified members of the IRF gene family that can activate transcription of the type I IFN gene in the absence of IRF-1.

For the IFN-inducible genes 2'-5' OAS, PKR, 1–8, and H2-K$^b$, kinetic studies showed no significant difference between embryonic fibroblasts from IRF-1 deficient and the wild type mice. Recent evidence has suggested that ISGF-3 plays the primary role in the transcription of IFN-inducible genes (reviewed by Levy and Darnell, 1991; Fu et al., 1992; Schindler et al., 1992). Hence, one possibility will be that IFN-inducible genes could be driven solely by ISGF-3 in the absence of IRF-1. However, each IFN-inducible gene has a unique 5' promoter configuration surrounding the ISRE, and variations in these sequences may modulate the affinities of different IFN-inducible genes for IRF-1 and ISGF-3 (reviewed by Stark and Keer, 1992); that is, the possibility cannot be excluded that some IFN-inducible genes not examined here may be more affected by the absence of IRF-1. It is also possible that a factor dependency for a given gene may differ in different cell types. Thus, the significance of IRF-1 in the activation of certain IFN-inducible genes in a variety of tissues needs further clarification.

IRF-1 is Involved in the Development of CD8⁺ T cells

Molecular mechanisms which govern T cell selection processes in the thymus are dependent on physiological contact between MHC molecules expressed on stromal cells and the T cell receptor (TcR) complex on developing thymocytes. Recognition of MHC class II molecules determines the generation of CD4⁺ T cells while interaction with MHC class I molecules commit thymocytes to CD8⁺ T cells (Zinkernagel et al., 1978; reviewed by Rothenberg, 1992; von Boehmer and Kisielow, 1993). Interaction between immature T cells and self MHC molecules on stromal cells and consequent maturation of CD4-single positive or CD8-single positive thymocytes are the basis for positive selection. Developing T cells which recognize self-peptides/MHC complexes with high affinity are negatively selected to maintain immunological tolerance. Recognition of MHC molecules by developing thymocytes must induce signal transduction through the TcR to the cytoplasm and nucleus which ultimately results in gene regulation by transcription factors (Ullman et al., 1990). It is, however, not known which signals mediated by the TcR determine T cell selection and lineage commitment; likewise, little is known about the role on transcription factors in thymocyte development. In fact, most of the previous studies on transcription factors have been carried out in mature T cells rather than thymocytes (Ivanov and Ceredig, 1992; Rothenberg, 1992), and T cell selection and lineage commitment during thymocyte ontogeny has not been addressed.

In IRF-1 deficient mice, the number of CD4⁺8⁺ and TcRαβ⁻CD4⁻8⁺ thymocytes was normal, while the number of TcRαβ⁺CD4⁻8⁺ T thymocytes was significantly reduced. Because the former two populations of thymocytes are recognized as precursors of TcRαβ⁺CD4⁻8⁺ T cells (Nickolic-Zugic et al., 1989; Guidos et al. 1989), these data show that IRF-1 deficient mice possess a lineage specific alteration in the development of mature TcRαβ⁺CD4⁻8⁺ T cell, that is, a block between the double positive and CD8-single positive, but not CD4-single positive stages. Differentiation of TcRαβ⁺CD4⁻8⁺ T cells from immature TcRαβ$^{dim}$CD4⁺8⁺ T cells has been shown to require interaction with class I MHC molecules. There is, however, no apparent difference in thymic staining pattern of MHC class I between wild type and IRF-1 deficient mice. In addition, MHC class I molecules are functional in IRF-1 deficient mice, as there is apparent CTL activity against LCMV-infected cells (which would require LCMV antigen associated with MHC class I on antigen presenting cells). Therefore, it is unlikely that expression of MHC class I is responsible for this phenotype, although we cannot exclude the possibility that thymic stroma cells cannot efficiently present functional MHC class I molecules to thymocytes in IRF-1 deficient mice.

A recent report has shown that bone marrow-derived progenitor T cells carry the maturation arrest between double positive and single positive T cells (Agui et al., 1991), and thus, not only the thymic environment but also an intrinsic defect in progenitor cells might explain the CD8⁺ T cell reduction in IRF-1 deficient mice. Interestingly, the promoter of the IL-7 receptor gene has a DNA element to which IRF-1 and IRF-2 have been shown to bind (Pleiman et al., 1991). As IL-7 has mitogenic activity on thymocytes (Everson et al., 1990), there is the possibility that an IL-7 receptor expression defect in IRF-1 deficient mice might cause poor expansion of CD8⁺ T cells. If this were the case, an IL-7 receptor expression defect would also have to affect CD8⁺ T cell lineage, because B cells and CD4⁺ T cells do not appear altered in the IRF-1 deficient mice. On the other hand, it should be noted that the IRF-1 gene is inducible by IFNs, IL-1, TNFs, IL-6, and LIF (Miyamoto et al., 1988; Fujita et al., 1989c; Pine et al., 1990; Abdollahi et al., 1991). Therefore, it is possible that perturbation of these cytokine systems would affect CD8⁺ T cell lineage commitment.

The reason for the CD8⁺ T cell reduction in IRF-1 deficient mice is unclear at present. T cell selection and lineage commitment are not fully understood processes. IRF-1 deficient mice will shed light on T cell ontogeny from the basis of transcriptional regulation.

Host Defence Mechanisms and IRF-1

IRF-1 deficient mice could mount a cytotoxic response against LCMV, although the activity was reduced. IRF-1 deficient mice also could produce neutralizing antibodies against VSV to the same extent as that of wild type mice. These data indicate that IRF-1 deficient mice can manage to survive some active infections. Long term observations of LCMV infection supports the notion that mice can survive after infection in the absence of IRF-1 (data not shown). On the other hand, fine tuned regulation of IRF-1 must be important. It is surprising that IRF-2 deficient mice died within 4 weeks of LCMV infection (data not shown), demonstrating that IRF-2 is essential for recovery from LCMV or possibly viral infection in general. Although the cause of lethality is not entirely understood, LCMV is not known to be harmful (Lehmann-Grube, 1982), suggesting that immunopathological mechanisms, not the virus itself, are involved. It appears that IRF-1 or factors having IRF-1 activity is responsible for this striking phenotype.

Experimental Procedures

Construction of Targeting Vector

Genomic DNA corresponding to the IRF-1 locus was isolated from a library of BALB/c mouse DNA (Miyatake et al., 1985). The 0.5 kb AccIII-PstI fragment (AccIII site was filled with T4 DNA polymerase) was cloned into pUC18 cleaved with SphI and PstI (SphI site was filled), to create plasmid pMIRF1PstI. The 1.1 kb BamHI-XhoI fragment of pMC1neoPolA (BamHI site was filled; Thomas and Capecchi, 1987) and the 3.1 kb BglII-BamHI fragment (BglII site was filled) containing exons 8 to 10 of the IRF-1 gene were ligated to pMIRF1PstI cleaved with SalI and BamHI. The resulting targeting vector was designated as pMIRF1neoB, containing 0.5 kb of 5' end and 3.1 kb of 3' end homology with the endogenous IRF-1 gene, and the neomycin resistance gene in the same transcriptional orientation as IRF-1.

Transfection and Selection of Mutant ES Cells

D3 embryonic stem cells (Doetschman et al., 1985) from 129/sv were maintained in Dulbecco's modified minimum essential medium (D-MEM) supplemented with 15% fetal calf serum, 5×10⁻⁵M of 2-mercaptoethanol, 2 mM of L-glutamine, and leukaemia inhibitory factor (LIF) (D3 medium), and subcultured every three days after complete trypsinization. Electroporation of embryonic stem cells and selection of G418-resistant colonies were carried out as described (Joyner et al., 1989). For PCR screening, medium was gently replaced with calcium-free, magnesium-free phosphate buffer saline (PBS⁻) and each G418-resistant colony was picked up with a 20 µl micropipette tip under microscopy, transferred to round bottomed 96 well plates (Nunc) filled with 100 µl of PBS⁻ per well. After transfer, 25 µl of 0.05% trypsin-0.53 mM EDTA (Gibco) was added followed by incubation for 10 minutes in a 37° C., 5% CO₂ incubator. Half aliquots of the resultant single cell suspension were again transferred to 96 well plates, each well containing 150 µl of D3 medium, left in a 37° C. CO₂ incubator overnight, and on the following day, the medium was replaced with 200 µl of D3 medium for further culture. Remaining cells in the 96 well plates were divided into half aliquots to duplicate 96 well plates for sib-selection by PCR. Two PCR primers for identifying IRF-1 homologous recombinations were used; IRF-1 sense oligonucleotide 5'TTC-CAGATTCCATGGAAGCACGC3' and neomycin resistant gene anti-sense oligonucleotide 5'ATTCGCCAATGACAA- GACGCTGG3'. PCR conditions used were 30 cycles of 94° C. for 30 seconds, 60° C for 30 seconds and 72° C. for 90 seconds. PCR positive clonies were subsequently confirmed by genomic Southern hybridization. Positive colones were stored in liquid nitrogen and thawed at least 3 days prior to blastocyst injection.

Generation of Mutant Mice

Generation of mutant mice from IRF-1 targeted ES cells were carried out as previously described (Hogan et al., 1986; Bradley et al. 1987). C57BL/6J blastocysts were isolated at day 3.5 post coitum (p.c.), injected with about 15 ES cells and transferred to the uteri of CD1 pseudopregnant recipient mice at day 2.5 p.c.. Newborn pups were identified as chimeric on the basis of agouti coat color and bred at 4 weeks of age with (C57BL/6Jx DBA/2) F1 or C57BL/6J. Germ line transmission was scored on the basis of agouti coat color of F1 pups 2 weeks after birth. Mutant gene transmission was confirmed by genomic Southern blotting of mouse tail DNA.

Gel Shift Assay

Gel shift analysis was performed as previously described (Harada et al., 1990)

Induction of Type I IFN mRNA

Poly(I):poly(C) (Yamasa shoyu) was added to embryonic fibroblasts in the presence of DEAE-dextran (Sigma) in D-MEM supplemented with 5% Nu-serum (Collaborative Research) for 1 hour. IFN induction with NDV was performed as previously described (Fujita et al., 1985).

Northern Blot Analysis

Total RNA was prepared as previously described (Harada et al. 1990). Probes for IFN-$\alpha$, IFN-$\beta$, and $\beta$-actin were prepared as previously described (Miyamoto et al., 1988). Probes for 2'5'OAS, 1–8, p65 double-stranded RNA dependent protein kinase (PKR), and H-2K$^b$ were prepared from a 1.4 kb EcoRI fragment of pMA25 (Yoshitake et al., 1986), a 0.2 kb EcoRI-HindIII fragment of Mu1-8 (Flenniken et al., 1988), a 1.0 kb EcoRI-BamHI fragment of murine p65 kinase (Feng et al., 1992), and a 1.0 kb PvuII-SacII fragment of pH202 (Reyes et al., 1982) cDNA respectively.

Flow Cytometric Analysis

Cells derived from lymphoid organs were singly suspended and 1×10$^6$ cells were stained on ice with monoclonal antibodies for 30 minutes in 200 µl of PBS—containing 1% bovine serum albumin and 0.1% sodium azide, washed with PBS and analyzed by FACScan (Becton Dickinson) using the Consort 30 or Lysis II program (Becton Dickinson). Monoclonal antibodies used were purchased from PharMingen except L3T4 (CD4) and Ly2 (CD8) (Becton Dickinson). For CD4$^+$T cell depletion, 5×10$^6$ thymocytes were suspended in 1 ml of Hanks BSS medium, and add 0.5 ml of monoclonal anti-CD4 antibody (RL172) supernatant was added, followed by the addition of 4 ml of Hanks BSS and 0.25 ml of complement (Low.Tox-M rabbit complement, Cederlane) and incubation at 37° C. for 1 hour. Samples were left on ice for 5 minutes to stop complement lysis and viable lymphocytes were isolated with 3 ml of lympholite-M (Cederlane).

CTL Assay

CTL assay was performed as previously described (Pircher et al., 1987; Ohashi et al., 1991)

Neutralizing Antibody Determination

VSV (Indiana strain) was injected intravenously (2×10$^6$ pfu per mouse) into 8 to 10 week old wild type mice and IRF-1 deficient mice. Blood samples were collected on day 4, 8, and 16 after infection. A neutralization assay was performed as previously described (Roost et al., 1988; Fung-Leung et al., 1991)

Histological Analysis

Tissues for haematoxylin-eosin staining were fixed in neutral buffered 5% formalin and processed. Tissues for immunohistochemistry were placed in a plastic bed filled with OCT compound medium (Miles Corp), submerged rapidly in liquid nitrogen and stored at −20° C. prior to microtome sectioning. Staining of MHC class I was performed with anti-H-2 haplotype supernatant (M1/42.3.9.8.HLK), or anti-H-2K$^b$ supernatant (B8-24-3), according to the method previously described (Shores et al., 1991).

Deposits

The ES cell line having the disrupted IRF-1 gene as shown in FIG. 1 has been deposited in the American Type Culture Collection, Rockville, Md., and given ATCC Accession No. CRL 11380.

References

Agui T, Sakai T, Himeno K, and Matsumoto K. (1991). Bone marrow-derived progenitor T cells convey the origin of maturational arrest from CD4$^+$CD8$^+$ to CD4$^+$CD8$^-$ thymocytes in LEC mutant rats. Eur. J. Immunol. 21, 2277–2280.

Abdollahi, A. K., Lord, B., Hoffman-Liebermann and Liebermann, D. A. (1991). Interferon regulatory factor-1 is a myeloid differentiation primary response gene induced by interleukin 6 and leukaemia inhibitory factor: role in growth inhibition. Cell Growth Differ. 2, 401–407.

Au, W.-C., Raj, N. K. B., Pine, R., and Pitha, P. M. (1992). Distinct activation of murine interferon-$\alpha$ promoter region by IRF-1/ISGF-2 and virus infection. Nucleic Acids Res. 20, 2877–2884.

Battegay, M., Cooper, S., Althage, A., Baenziger, J., Hengartner, H., and Zinkernagel, R. M. (1991). Quantification of lymphocytic choriomeningitis virus with an immunological focus assay in 24- or 96-well plates. J. Virol. Meth. 33, 191–198.

Bradley, A. (1987). Production and analysis of chimeric mice. In Teratocarcinomas and Embryonic Stem Cells, E. J. Robertson, ed. (Oxford, Washington, DC:IRL Press), 113–152.

Chan, S. H., Cosgrove D., Waltzinger C., Benoist C., and Mathis, D. (1993). Another view of the selective model of thymus selection. Cell 73, 225–236.

Chang, C. H., Hamer, J., Loh, J. E., Fodor, W. L., and Flavell, R., A. (1992). The activation of major histocompatibility complex class I genes by interferon regulatory factor-1 (IRF-1). Immunogenetics 35, 378–384.

David-Watine, B., Israël, A., and Kourilsky, P. (1990). The regulation and expression of MHC class I genes. Immunol. Today 11, 286–292.

De Maeyer, E., and De Maeyer-Guignard, J. (1988). Interferons and other regulatory cytokines. (New York: John Wiley & Sons).

Doetschman, T. C., Eistelter, H., Katz, M., Schmidt, W., and Kemler, R. (1985). The in vitro development of blastocyst-derived embryonic stem cell lines: formation of visceral yolk sac, blood islands and myocardium. J. Embryol. Exp. Morphol. 87, 27–45.

Driggers, P. H., Ennist, D. L., Gleason, S. L., Mak, W-H., Marks, M. S., Levi, B.-Z., Flanagan, J. R., Appella, E., and Ozato, K. (1990). An interferon-γ regulated protein that binds the interferon-inducible enhancer element of major histocompatibility complex class I genes. Proc. Natl. Acad. Sci. USA 87, 3743–3747.

Du, W., and Maniatis, T. (1992). An ATF/CREB element is required for virus induction of the human interferon-$\beta$ gene. Proc. Natl. Acad. Sci. USA 89, 2150–2154.

Enoch, T., Zinn K., and Maniatis T. (1986). Activation of the human β-interferon gene requires an interferon-inducible factor. Mol. Cell.Biol. 6, 801–810.

Everson, M. P., Eldrige, J. H., and Koopman, W. J. (1990). Synergism of Interleukin 7 with thymocyte growth factors interleukin 2, interleukin 6, and tumor necrosis factor α in the induction of thymocyte proliferation. Cell Immunol. 127, 470–482.

Feng, G.-S., Chong, K., Kumar, A., and Williams, B. R. G. (1992). Identification of double-stranded RNA-binding domains in the interferon-induced double-stranded RNA-activated p68 kinase. Proc. Natl. Acad. Sci. USA 89, 5447–5451.

Flenniken, A., Galabru, J., Rutherford, M. N., Hovanessian, A. G., and Williams, B. R. G. (1988). Expression of interferon-induced genes in different tissues of mice. J. Virol. 62, 3077–3083.

Fu, X-Y., Schindler, C., Improta, T., Aebersold, R., and Darnell, Jr. J. E. (1992). The proteins of ISGF-3, the interferon α-induced transcriptional activator, define a gene family involved in signal transduction. Proc. Natl. Acad. Sci. USA 89, 7840–7843, 1992

Fujita, T., Ohno, S., Yasumitsu, H., and Taniguchi, T. (1985). Delimitation and properties of DNA sequences required for the regulated expression of human interferon-β gene. Cell 41, 489–496.

Fujita, T., Shibuya, H., Hotta, H., Yamanishi, K. and Taniguchi, T. (1987). Interferon-β gene regulation: tandemly repeated sequences of a synthetic 6 bp oligomer function as virus-inducible enhancer. Cell 49,357–367.

Fujita, T., Sakakibara, J., Sudo, Y., Miyamoto, M., Kimura, Y., and Taniguchi, T. (1988). Evidence for a nuclear factor(s), IRF-1, mediating induction and silencing properties to human IFN-β gene regulatory elements. EMBO J. 7, 3397–3405.

Fujita, T., Miyamoto, M., Kimura, Y., Hammer, J., and Taniguchi, T. (1989a). Involvement of a cis-element that binds an H2TF-1/NF-κB like factor(s) in virus-induced interferon-β gene expression. Nucleic Acids Res. 17, 3335–3346.

Fujita, T., Kimura, Y., Miyamoto, M., Barsoumian, E. L., and Taniguchi, T. (1989b). Induction of endogenous IFN-α and IFN-β genes by a regulatory transcription factor, IRF-1. Nature 337, 270–272.

Fujita, T., Reis, L., Watanabe, N., Kimura, Y., Taniguchi, T., and Vilček, J. (1989c). Induction of the transcription factor IRF-1 and interferon-β mRNAs by cytokines and activators of second messenger pathways. Proc. Natl. Acad. Sci. USA 86, 9963–9940.

Fung-Leung W-P, Schilham M. W., Rahemtulla A., K ündig T. M., Vollenweider M., Potter J., van Ewijk W., and Mak T. W. (1991). CD8 is needed for development of cytotoxic T cells but not helper T cells. Cell 65, 443–449.

Guidos, C. J., Weissman, I. L., and Adkins, B. (1989). Intrathymic maturation of murine T lymphocytes from CD8+ precursors. Proc. Natl. Sci. USA 86, 7542–7546.

Gupta, S. C., Hengartner, H., and Zinkernagel, R. M. (1986). Primary antibody responses to a well-defined and unique hapten are not enhanced by preimmunization by carrier: analysis in a viral model. Proc. Natl. Sci. USA 83, 2604–2608.

Harada, H., Fujita, T., Miyamoto, M., Kimura, Y., Maruyama, M., Furia, A., Miyata, T., and Taniguchi, T. (1989). Structurally similar but functionally distinct factors, IRF-1 and IRF-2, bind to the same regulatory elements of IFN and IFN-inducible genes. Cell 58, 729–739.

Harada, H., Willison, K., Sakakibara, J., Miyamoto, M., Fujita, T., and Taniguchi, T. (1990). Absence of type I interferon system in EC cells: transcriptional activator (IRF-1) and repressor (IRF-2) genes are developmentally regulated. Cell 63, 303–312.

Harada, H., Kitagawa, M., Yamamoto, H., Harada, K., and Taniguchi, T. (1993). Anti-oncogenic and oncogenic potentials of transcriptional regulators IRF-1 and IRF-2: A link between the interferon system and cell growth control. Science, 259, 971–974.

Hogan, B., Costantini, F., and Lacy, E. (1986). Manipulating the Mouse Embryo: A Laboratory Manual (Cold Spring Harbour, New York: Cold Spring Harbour Laboratory).

Ivanov, V., and Ceredig, R. (1992). Transcription factors in mouse fetal thymus development. International Immunol. 4, 729–737.

Joyner, A., Skarnes, W. C., and Rossant, J. (1989). Production of a mutation in mouse En-2 gene by homologous recombination in embryonic stem cells. Nature 338, 153–155.

Kaer L. V., Ashton-Rickardt P. G., Ploegh H. L., and Tonegawa S. (1992). TAP1 mutant mice are deficient in antigen presentation, surface class I molecules, and CD4− CD8+ T cells. Cell 71, 1205–1214.

Koller, B. H., Marrack, P., Kappler, J. W., and Smithies, O. (1990). Normal development of mice deficient in $\beta_2$M, MHC class I proteins, and CD8+ T cells. Science 248, 1227–1230.

Korber, B., Mermod, N., Hood, L., and Stroynowski, I. (1988). Regulation of gene expression by interferons: control of H-2 promoter responses. Science 239, 1302–1306.

Leblanc J-F., Cohen L., Rodrigues M., and Hiscott J. (1990). Synergism between distinct enhanson domains in viral induction of human beta Interferon gene. Mol. cell. Biol. 10, 3987–3993.

Lehmann-Grube, F. (1982). Lymphocytic choriomeningitis virus. The mouse in biomedical research, Vol II, Diseases, H. L., Foster, D., Small, and J. D. Fox, eds. (New York: Academic Press), pp. 231–266.

Lenardo, M. J., Fan, T., Maniatis, T., and Baltimore, D. (1989). The involvement of NF-kappa B in beta-interferon gene regulation reveals its role as widely inducible mediator of signal transduction. Cell 57, 287–294.

Levy, D. and Darnell, J., E., Jr. (1990). Interferon-dependent transcriptional activation: Signal transduction without second messenger involvement? New Biologist 2, 383–392.

MacDonald, N.J., Kuhl, D., Maguire D., Näf, D., Gallant, P., Goswamy, A., Hug, H., Bueler H., Chaturvedi, M., de la Fuente, J., Ruffner, H., Meyer, F., Weissmann C. (1990). Different pathways mediate virus inducibility of the human IFN-α1 and IFN-β genes. Cell 60, 767–779.

Miyamoto, M., Fujita, T., Kimura, Y., Maruyama, M., Harada, H., Sudo, Y., Miyata, T., and Taniguchi, T. (1988). Regulated expression of a gene encoding a nuclear factor, IRF-1, that specifically binds to IFN-beta gene regulatory elements. Cell 54, 903–913.

Miyatake, S., Yokota, T., Lee, F., and Arai, K. (1985). Structure of the chromosomal gene for murine interleukin 3. Proc. Natl. Acad. Sci. USA 82, 316–320.

Näf, D., Hardin, S. E., and Weissmann, C. (1991). Multimerization of AAGTGA and GAAAGT generates sequences that mediate virus inducibility by mimicking an interferon promoter element. Proc. Natl. Acad. Sci. USA 88, 1369–1373.

Namen, A. E., Schmierer, A. E., March, C. J., Overell, R. W., Park, L. S., Urdel, D. L., and Mochizuki, D. Y. (1988). B cell precursor growth promoting activity. Purification and characterization of a growth factor active on lymphocyte precursors. J. Exp. Med. 167, 988–1002.

Nikolic-Zugic, J., Moore, M. W., and Bevan, M. J. (1989). Characterization of the subsets of immature thymocytes which can undergo rapid in vitro differentiation. Eur. J. Immunol. 19, 649–653.

Ohashi, P. S., Oehen, S., Buerki, K., Pircher, H., Ohashi, C. T., Odermatt, B., Malissen, B., Zinkernagel, R. M., and Hengartner, H. (1991). Ablation of "tolerance" and induction of diabetes by virus infection in viral antigen transgenic mice. Cell 65, 305–317.

Palombella, V. J., and Maniatis, T. (1992). Inducible processing of interferon regulatory factor-2. Mol. Cell. Biol. 12, 3325–3336.

Pine, R., Levy, D. E., Reich, N., and Darnel, J. E., Jr. (1990). Purification and cloning of interferon-stimulated gene factor 2 (ISGF2): ISGF2 (IRF-1) can bind to the promoters of both beta interferon and interferon-stimulated genes but not a primary transcriptional activator of either. Mol. Cell. Biol. 10, 2448–2457.

Pine, R. (1992). Constitutive expression of an ISGF2/IRF1 transgene leads to interferon-independent activation of interferon-inducible genes and resistance to virus infection. J. Virol. 7, 4470–4478.

Pircher, H. P., Baenziger, J., Schilham, M., Sado, T., Kamisaku, H., Hengartner, H., and Zinkernagel, R. M. (1987). Characterization of virus-specific cytotoxic T cell clones from allogenic bone marrow chimeras. Eur. J. Immunol. 17, 159–166.

Pleiman, C. M., Gimpel, S. D., Park, L. S., Harada, H., Taniguchi, T., and Ziegler, S. F. (1991). Organization of the murine and human interleukin-7 receptor genes: two mRNAs generated by differential splicing and presence of a type I interferon-inducible promoter. Mol. Cell. Biol. 11, 3052–3059.

Reis, L. F., Harada, H., Wolchok, J. D., Taniguchi, T., and Vilcek, J. (1992). Critical role of a common transcription factor, IRF-1, in the regulation of IFN-β and IFN-inducible genes. EMBO J. 11, 185–193.

Reyes, A.A., Schöld, M., Itakura, K., and Wallace, R. B. (1982). Isolation of a cDNA clone for the murine transplantation antigen H-2K$^b$. Proc. Natl. Sci. USA 79, 3270–3274.

Roost, H., Charan, S., Gobet, R., Rüedi, E., Hengartner, H., Althage, A., and Zinkernagel, R. M. (1988). An acquired immune suppression in mice caused by infection with lymphocytic choriomeningitis virus. Eur. J. Immunol. 18, 511–518.

Rosenberg, E. V. (1992). The development of functionally responsive T cells. Advance in Immunolgy 51, 85–214.

Rudnicki M., Braun T., Hinuma S., Jaenisch R. (1992). Inactivation of MyoD in mice leads to up-regulation of the myogenic HLH gene Myf-5 and results in apparently normal muscle development. Cell 71, 383–390.

Scolley, R., Bartlett, P., and Shortman, K. (1984). T cell development in the adult murine thymus: Changes in the expression of the surface antigen Ly2, L3T4, and B2A2 during development from early precursor cells to emigrants. Immunol. Rev. 82, 79–103.

Sen, G. C. and Ranshoff R. M. (1993). Interferon-induced antiviral actions and their regulation. Advance in Virus Research 42, 57–102

Shores, E. W., van Ewijk, W., and Singer, A. (1991). Disorganization and restoration of thymic medullary epithelial cells in T cell receptor-negative scid mice, evidence that receptor bearing lymphocytes influence maturation of the thymic microenvironment. Eur. J. Immunol. 21, 1657–1661.

Stark, G. K., and Kerr, I. M. (1992). Interferon dependent signalling pathways: DNA elements, transcription factors, mutations, and effects of viral proteins. J. Interferon Res. 12, 147–151.

Stewart II, W. E., Gosser, H. L. B., and Lockart, R. Z. (1971). Priming: a nonantiviral action of interferon. J.Virol. 7, 792–801.

Stewart II, W. E. (1979). Priming. In The Interferon System (New York: Springer-Verlag). pp. 233–236.

Tanaka, N., Kawakami, T., and Taniguchi, T. (1993). Recognition DNA sequences of interferon regulatory factor-1 (IRF-1) and IRF-2, regulators of cell growth and the interferon system. Mol. Cell. Biol. in press.

Thomas, K. R., and Capecchi, M. R. (1987). Site-directed mutagenesis by gene targeting in mouse embryo-derived stem cells. Cell 51, 503–512.

Uegaki, K., Shirakawa, M., Fujita, T., Taniguchi, T., and Kyougoku, Y. (1993). Characterization of the DNA binding domain of the mouse IRF-2 protein. Protein Engineering 6, 195–200.

Ullman, K. S., Northrop, J. P., Verweij, C. L., and Crabtree, G. R. (1990). Transmission of signals from the T lymphocytes antigen receptor to the genes responsible for cell proliferation and immune function: The missing link. Ann. Rev. Immunol. 8, 421–451.

Veals, S. A., Schindler, C., Leonard, D., Fu, X.-Y., Aebersold, R., Darnell, J- E., Jr. and Levy, D. E. (1992). Subunit of an alpha-interferon-responsive transcription factor is related to interferon regulatory factor and Myb families of DNA-binding proteins. Mol. Cell. Biol. 12, 3315–3324.

Vilcek, J. (1990). Interferons. In Peptide Growth Factors and Their Receptors. Handbook of Experimental Pharmacology, M. A. Sporn and B. Roberys, eds. (Berlin: Springer-Verlag), pp. 3–38.

Visvanathan, K. V., and Goodbourn, S. (1989). Double-stranded RNA activates binding of NFκB to an inducible element in human β-interferon promoter. EMBO J. 8, 1129–1138.

von Boehmer, H. and Kisielow, P. (1993). Lymphocyte lineage commitment: instruction versus selection. Cell 73, 207–208.

Weisz, A., Marx, P., Sharf, R., Appella, E., Driggers, P. H., Ozato, K., and Levi, B-Z. (1992). Human interferon consensus sequence binding protein is a negative regulator of enhancer elements common to Interferon-inducible genes. J.Biol.Chem. 267, 25589–25596.

Whittemore, L. A., and Maniatis, T. (1990). Postinduction repression of the beta-interferon gene is mediated through two positive regulatory domains. Proc. Natl. Acad. Sci. USA 87, 7799–7803.

Williams B. R. G. (1991). Transcriptional regulation of interferon-stimulated genes. Eur.J.Biochem. 200, 1–11.

Willman, G. L., Sever, C. E., Pallavicini, M. G., Harada, H., Tanaka, N., Slovak, M. L., Yamamoto, H., Harada, K., Meeker, T. C., List, A. F., and Taniguchi, T. (1993). Deletion of IRF-1, mapping to chromosome 5q31.1, in human leukaemia and preleukemia myelodysplasia. Science 259, 968–971.

Yamada, G., Ogawa, M., Akagi, K., Miyamoto, H., Nakano, N., Itoh, S., Miyazaki, J.-I., Nishikawa, S.-I., Yamamura, K., and Taniguchi T. (1991). Specific depletion of the B-cell population induced by aberrant expression of human interferon regulatory factor 1 gene in transgenic mice. Proc. Natl. Acad. Sci. USA 88, 532–536.

Yoshitake, I., Fukunaga, R., Shiojiri, S., and Sokawa, Y. (1986). Mouse 2-5A synthetase cDNA: nucleotide sequence and comparison to human 2-5A synthetase. Nucl. Acids Res. 14, 10117.

Zijlstra, M., Bix, M., Simister, N. E., Loring, J. M, Raulet, D. H., and Jaenisch, R. (1990). β2-microglobulin deficient mice lack CD4$^-$8$^+$ cytolytic T cells. Nature 344, 742–746.

Zinkernagel, R. M., Callahan, G. N., Althage, A., Cooper, S., Klien, P. A., and Klien, J. (1978). On the thymus in the differentiation of H-2 self recognition by T-cells: Evidence for dual recognition. J. Exp. Med. 147, 882–896.

Zinkernagel R. M., and Hengartner H. (1992). Virally induced immunosuppression. Current Opinion in Immunology, 4, 408–412.

We claim:

1. A mutant mouse comprising disrupted Interferon Regulatory Factor-1 (IRF-1) genes, a disruption in said genes having been introduced into the mouse or an ancestor of the mouse at an embryonic stage, wherein the disruption prevents the synthesis of functional IRF-1 in cells of the mouse and results in the mutant mouse having a reduced number of $CD4^-8^+$ T cells compared to the number of $CD4^-8^+$ T cells in a mouse lacking disrupted IRF-1 genes.

2. A mouse as claimed in claim 1, wherein said disruption is introduced by homologous recombination, said homologous recombination resulting in the insertion of a marker gene encoding a selectable in the IRF-1 gene, thereby disrupting the coding sequence of said IRF-1 gene.

3. The mouse of claim 2 wherein said disruption is introduced with a DNA construct comprising:

exons 3 and 8–10 of the IRF-1 gene; and a neomycin resistance gene inserted between exon 3 and exons 8–10 of the IRF-1 gene, said neomycin resistance gene being in the same transcriptional orientation as exons 3, 8, 9, and 10 of the IRF-1 gene, and wherein said construct lacks exons 4–7 of the IRF-1 gene.

4. A mouse as claimed in claim 3, wherein the construct is inserted into embryonic stem cells by electroporation, and neomycin resistant colonies are identified for said homologous recombination by cellular DNA screening using a polymerase chain reaction.

5. A mouse as claimed in claim 1, wherein the number of $TcR\alpha\beta^+CD4^-CD8^+$ T cells is about 10-fold less in peripheral blood, spleen, lymph nodes and thymus as compared to wild type mice.

6. The embryonic stem (ES) cell line having a disrupted IRF-1 gene and having ATCC Accession No. CRL 11380.

* * * * *